(12) United States Patent
Bovin et al.

(10) Patent No.: US 7,294,615 B1
(45) Date of Patent: Nov. 13, 2007

(54) COMPOUNDS THAT ASSOCIATE ON THE INTERMOLECULAR LEVEL AND AGGREGATE BODIES THAT CONTAIN THEM

(75) Inventors: Nikolai Vladimirovich Bovin, 117871 Moskow ul. Artsimovicha 11 kv. 181, Moskow (RU); Alexander Borisovich Tusikov, Moskow (RU); Alexander Alexandrovich Chinarev, Moskow (RU); Maria Alexandravona Dicusar, Moskow (RU); Alexandra Sergeevna Gambarian, Moskow (RU); Valentina Petrovna Marinina, 117321 Moskow ul. Profsojuznaya 140/2, kv. 273, Moskow (RU)

(73) Assignees: Nikolai Vladimirovich Bovin, Moscow (RU); Alexandr Borisovich Tusikov, Moscow (RU); Alexandr Alexandrovich Chinarev, Moscow (RU); Maryia Alexandrovna Dicusar, Moscow (RU); Alexandra Sergeevna Gambariyan, Moscow (RU); Valentina Petrovna Marinina, Moscow (RU)

( * ) Notice: Subject to any disclaimer, the term of this patent is extended or adjusted under 35 U.S.C. 154(b) by 0 days.

(21) Appl. No.: 10/019,902

(22) PCT Filed: Jun. 30, 2000

(86) PCT No.: PCT/EP00/06139

§ 371 (c)(1),
(2), (4) Date: Jul. 2, 2002

(87) PCT Pub. No.: WO01/02018

PCT Pub. Date: Jan. 11, 2001

(30) Foreign Application Priority Data

Jun. 30, 1999 (DE) ................................ 199 30 177

(51) Int. Cl.
*A61K 38/10* (2006.01)
*A61K 38/16* (2006.01)
(52) U.S. Cl. .............................. 514/8; 514/12; 514/13; 514/14; 514/15; 514/16; 514/17; 530/325; 530/326; 530/327; 530/328; 530/329; 530/330
(58) Field of Classification Search .................... 514/8, 514/12–17; 530/325–330
See application file for complete search history.

(56) References Cited

U.S. PATENT DOCUMENTS 5,243,035 A  9/1993 Nakabayashi et al. ....... 536/4.1
6,676,946 B2 * 1/2004 Bay et al. ............... 424/196.11

FOREIGN PATENT DOCUMENTS

EP           0601417  A2   6/1994
EP            747063        12/1996
WO       WO 93/17033        9/1993
WO       WO 94/06467        3/1994
WO       WO 96/26933        9/1996
WO       WO 97/31006        8/1997
WO       WO 98/142015  *    4/1998
WO       WO 00/55149        9/2000

OTHER PUBLICATIONS

Tuzikov, A. B., et al "Polyglycine II nanosheets" ChemBioChem (2003) vol. 4, pp. 147-154.*
Mammen, M. et al "Polyvalent interactions in biological systems . . . " Angew. Chem. Int. Ed. (1998) vol. 37, pp. 2754-2794.*
CAS abstract document No. 121:109622. (1994).*
Watowich, S. et al "Crystal structures of influenza virus hemagglutinin . . . " Structure (1994) vol. 2, pp. 719-731.*
CAS abstract document No. 122:99869. (1994).*
International Search Report for PCT/AU00/00165 dated Apr. 5, 2000.

(Continued)

*Primary Examiner*—Leigh C. Maier
(74) *Attorney, Agent, or Firm*—Myers Bigel Sibley & Sajovec, P.A.

(57) ABSTRACT

Compound of the general formula (I)

$$X(B)_m \qquad (I)$$

wherein
X is an m-valent unit and
B are identical or different and denote K-R, wherein
  K is a bond or is $A^1$—$(A^2$—$A^3)_k$-sp, wherein
    $A^1$ is $(CH_2)_t Y(CH_2)_u$, wherein
    Y is >C=O, >NH, —O—, —S— or a bond,
    t is an integer from 0 to 6 and
    u is an integer from 0 to 6,
    $A^2$ is —NHCO—, —CONH—, —OCONH— or SCONH—, or is —CO—,
    $A^3$ is $(CH_2)_r$, $O(CH_2)_r$, $NH(CH_2)_r$, $S(CH_2)_r$ or —(CHQ)—, wherein
    r is an integer from 1 to 6 and
    Q is a substituted or unsubstituted alkyl or aryl group,
    sp is a divalent spacer or a bond, and
    k is an integer from 5 to 100, and
  R is hydrogen; a ligand suitable for specific bonding to a receptor; a marker molecule; or a catalytically active group; and
  m is at least 2,
with the proviso that
(1) in the compound at least one R is not hydrogen,
(2) there are at least two K that are not a bond, and
(3) X, B and m are so selected that an intermolecular association of the K in liquid phase by the formation of hydrogen bonds is possible, with formation of aggregates that present on the surface a plurality of R that are not hydrogen, and
(4) the molar mass of the fragment $X(K)_m$ is less than 20,000.

14 Claims, 3 Drawing Sheets

OTHER PUBLICATIONS

Meindl et al., "Inhibition of Neuraminidase Activity by Derivatives of 2-Deoxy-2,3-dehydro-N-acetyl-Neuraminic Acid," *Virology* 58: 457-463 (1974).

Meindl et al., "Synthese und Eigen schaften von 2-Deoxy-2,3-dehydroneuraminsaure sowie neuer N-Acylderivative," *Monatschefie fur Chemie* 104: 402-414 (1973).

Choi et al. (1997) "Generation and in Situ Evaluation of Libraries of Poly (acrylic acid) Presenting Sialosides as Side Chains as Polyvalent Inhibitors of Influenza-Mediated Hemagglutination" *J. Am. Chem. Soc.* 119:4103-4111.

Chow et al. (1998) "The Synthesis and Properties of Novel Functional Dendritic Molecules" *Tetrahedron* 54:8543-8660.

Feofanov et al. (1997) "Study of Sialylated Neoglycoconjugates by Surface-Enhanced Raman Scattering Spectroscopy" 23:910-918 (Abstract in English Only).

Gambaryan et al. (1997) "Specification of Receptor-Binding Phenotypes of Influenza Virus Isolates from Different Hosts Using Synthetic Sialylglycopolymers: Non-Egg-Adapted Human H 1 and H3 Influenza A and Influenza B Viruses Share a Common High Binding Affinity for 6'-Sialyl(N-acetyllactosamine)" *Virology* 232:345-350.

Kretzschmar et al. (1995) "Oligosaccharide Recognition by Selectins: Synthesis and Biological Activity of Multivalent Sialyl Lewis-X Ligans" *Tetrahedron* 51:13015-13030.

Nishimura et al. (1994) "Chemoenzymic Preparation of a Glycoconjugate Polymer Having A Sialylogiosaccharide: Neu5Acα(2→3)Galβ(1→4)GlcNAc" *Biochemical and Biophysical Research Communications* 199:249-254.

Reuter et al. (1999) "Inhibition of Viral Adhesion and Infection by Sialic-Acid-Conjugated Dendritic Polymers" *Bioconjugate Chem.* 10:271-278.

Reuter et al. (1998) "Sialic Acid Conjugated Dendritic Polymers Inhibit Influenza Virus Binding to Target Cells in a Strutural and Virus Strain-Specific Manner" *Antimicrobial Chemotherapy* 98:51 (abstract only).

Roy et al. (1993) "Solid-phase Synthesis of Dendritic Sialoside Inhibitors of Influenza A Virus Haemagglutinin" *J. Chem. Soc. Chem. Comm.* 24:1869-1872.

Unverzagt et al. (1994) "Chemical and enzymatic synthesis of multivalent sialoglycopeptides" *Carbohydr. Res.* 251:285-301.

Yamada et al. (Dec. 1997) "High performance polymer supports for enzyme-assisted synthesis of glycoconjugates" *Carbohydr. Res.* 305:443-461.

Wu et al. (2000) "Synthesis of a Polymeric 4-N-linked Sialoside which Inhibits Virus Hemagglutinin" *Bioorganic & Medicinal Chemistry Letter* 10:341-343.

Zanini et al. (1996) "Novel Dendritic α-Sialosides: Synthesis of Glycodendrimers Based on a 3, 3 '-Iminobis(propylamine) Core" *J. Org. Chem.* 61:7348-7354.

International Search Report for PCT Application No. PCT/EP00/06139, mailed Oct. 9, 2001.

Guedj, C. et al. (1995) "Vesicles and other supramolecular systems from biocompatible synthetic glycolipids with hydrocarbon and/or fluorocarbon chains" Abstract in *Chemical Abstracts,* 122: 1099.

Kopecek, Jindrich et al. (1995) "Drug-delivery polymers and pharmaceutical compositions employing them" Czech Republic Patent No. CZ 278,551, Abstract in *Chemical Abstracts*, 122:600.

Lio, Raul Gonzalez et al. (1999) "Chemoenzymatic Synthesis of Spacer-Linked Oligosaccharides for the Preparation of Neoglycoproteins." *Carbohydrate Research*, 317:180-190.

Sabesan, Subramaniam et al. (1992) Cluster Sialoside Inhibitors for Influenza Virus: Synthesis, NMR, and Biological Studies. *Journal of the American Chemical Society,* 114:8363-8375.

Shimizu, Toshimi. (1999) "Noncovalent synthesis and structural properties of supramolecular polymer architectures from bola-form amphiphiles" Abstract in *Chemical Abstracts,* 130(20): 293.

Zanini, Diana et al. (1998) Practical Synthesis of Starburst PAMAM α-Thiosialodendrimers for Probing Multivalent Carbohydrate-Lectin Binding Properties. *Journal of Organic Chemistry,* 63: 3486-3491.

\* cited by examiner

Elution profiles of aggregates {[Neu5Ac-Gab-AC$_m$-Ad-Gly$_5$-NHCH$_2$-]$_4$C}$_x$, HPLC, TSK-4000, 0.2 M NaCl Relative particle size distribution of aggregate
{[Neu5Ac-Gab-Ad-AC$_3$-Gly$_5$-NHCH$_2$-]$_4$C}$_x$, 20°C H$_2$O Influence of temperature and of the presence of urea on the particle size of aggregate $\{[\text{Neu5Ac-Gab-Ad-Gly}_7\text{-NHCH}_2\text{-}]_4 C\}_x$

COMPOUNDS THAT ASSOCIATE ON THE INTERMOLECULAR LEVEL AND AGGREGATE BODIES THAT CONTAIN THEM

CROSS-REFERENCE TO RELATED APPLICATIONS

The present application is a U.S. national phase application of PCT International Application No. PCT/EP00/06139 (published under PCT Article 21(2) in German), filed on Jun. 30, 2000, which claims priority to German Patent Application 199 30 177.8, filed Jun. 30, 1999, the disclosures of which are incorporated herein by reference in their entirety.

The present invention relates to special low molecular weight compounds suitable for forming aggregates by intermolecular association. The present invention relates also to aggregates comprising such compounds, and to processes for the preparation of such aggregates. The invention relates also to special uses of the compounds and aggregates, especially for therapeutic and diagnostic purposes.

The simultaneous and specific association of at least two ligands with corresponding receptors results in multivalent interactions between two units carrying those ligands or receptors. Such multivalent interactions are very widespread in biology, it being possible for the interacting units to have ligands such as oligosaccharides, proteins, nucleic acids or lipids. Multivalent interactions are characterised by a large number of individual weak monovalent bonds which in biological systems are frequently preferred over a single strong monovalent bond (M. Mammen, S-K. Choi, G. M. Whitesides, *Angew. Chemie*, 110, 2908, 1998).

In biological systems, multivalent interactions are frequently developed when bonds are formed between units with ligands and receptors having little affinity. Known examples of interactions between ligands and receptors having little affinity are carbohydrate-protein and carbohydrate-carbohydrate interactions (A. Danguy, K. Kayser, N. V. Bovin, H.-J. Gabius, *Trends Glycosc. Glycotech.*, 7, 261, 1995), which, for example, in viral and bacterial infections play a crucial role in the onset of inflammatory processes, in the formation of tumour metastases or in immunorecognition.

Natural multivalent interactions can be blocked especially for therapeutic and diagnostic purposes. For the in vitro blocking of such multivalent interactions, both monovalent and multivalent inhibitors have been used hitherto.

In the case of derivatives of natural ligands as monovalent inhibitors it has been shown in practice that as a result of the low binding affinity it is not possible to achieve efficient inhibition of multivalent interactions. For example, the binding constant in the case of interaction between a monovalent galactoside and the corresponding lectin is only $K_D \sim 10^4 M$ (D. T. Connolly et al., *J. Biol. Chem.*, 257, 939, 1982). For therapeutic use in such a case, very large amounts of inhibitor would have to be used. A method of treatment using such an inhibitor would not therefore be cost-effective.

Known multivalent inhibitors include those in which a plurality of ligands are covalently bonded to a low molecular weight carrier (L. L. Kiesling, N. L. Pohl, *Chemistry & Biology*, 3, 71, 1996; G. D. Glick, P. L. Toogood, D. C. Wiley, J. J. Skehel, J. R. Knowles, *J. Biol. Chem.*, 266, 23660, 1991) or to a dendrimer (D. Zanini, R. Roy, *J. Org. Chem.*, 63, 3486, 1998). In those cases, however, the specific binding affinity is only very slightly increased.

WO 98/14215 discloses glucoconjugates as inhibitors of viral cell adhesion. In particular, the compound [Neu5Acα2-6Galβ1-4GlcNAcβ1-NHCOCH$_2$NH—CO(CH$_2$)$_4$CO—(NHCH$_2$—CO)$_3$—NHCH$_2$—]$_4$C is disclosed. That compound does not, however, form aggregates in aqueous solution.

Also known are multivalent inhibitors in which the active ligands are bonded to a polymeric carrier. Such compounds exhibit increased efficiency in comparison with the corresponding monomeric ligands. By way of the example of the interaction between the influenza-haemagglutinin, which binds to neuraminic acid derivatives on the cell surface, it has been shown how the use of a polymer-based multivalent inhibitor affects that interaction (monovalent: $K_D \sim 2 \times 10^{-4} M$, multivalent: $K_D \sim 3 \times 10^{-7} M$; A. Spaltenstein et al., *J. Am. Chem. Soc.*, 113, 686, 1991).

Despite their improved effectiveness, the multivalent polymeric inhibitors known hitherto are also unsuitable for therapeutic use. The disadvantages are to be attributed to the polymeric carrier molecules used and to the properties thereof.

When polylysine or sulfated polysaccharides are used as polymeric carriers, non-specific ionic interactions with cell surface structures take place.

Polyacrylamides and other polymers, the polymer content of which consists exclusively of C—C bonds, have the crucial disadvantage that they are broken down in the organism to form toxic metabolites.

High polymers (60-70 kDa) are not effectively filtered by the kidneys and their breakdown by the liver can lead to intolerances as a result of the formation of toxic metabolites.

Patent applications EP 601 417 and WO 95/34673 describe polymer-based carbohydrate receptor blockers that are physiologically tolerable both in the form of the total molecule and in the form of breakdown products. Those properties are achieved by the use of bio-degradable polymers. For use as a medicament, however, those products too have a fundamental disadvantage because, in practice, polymers are not pure and precisely defined compounds, but rather consist of complex mixtures of compounds of different molecular size. This circumstances renders the use (approval) of such a polymeric inhibitor as a medicament extraordinarily difficult.

In the case of a medicament it is important to have accurate knowledge of the associations between the chemical structure of an active ingredient and its pharmacological properties. In the case of substance mixtures, it would have to be shown in what way the composition of a mixture influences its particular pharmacological properties. In addition, a medicament must be precisely defined in its chemical composition and must be demonstrably preparable in precisely that form. Neither requirement can be fulfilled in the case of the polymeric multivalent inhibitors using the synthetic and analytical methods currently available and using a technically sensible level of resources.

A further group of multivalent inhibitors comprises compounds wherein the ligands are bonded to the surface of liposomes. Liposomes have the disadvantage that their lipophilic constituents are able to enter into non-specific interactions, for example by being incorporated into cell membranes.

The problem underlying the present invention is therefore to avoid the disadvantages of the prior art and to make available new compounds having improved properties as multivalent inhibitors of biological recognition processes, the compounds having a specific action and being suitable for use as medicaments.

That problem is solved in accordance with the claims using a compound of the general formula (I)

$$X(B)_m \quad (I)$$

wherein

X is an m-valent unit and

B are identical or different and denote K-R, wherein

K is a bond or is $A^1-(A^2-A^3)_k$-sp, wherein $A^1$ is $(CH_2)_tY(CH_2)_u$, wherein Y is >C=O, >NH, —O—, —S— or a bond, t is an integer from 0 to 6 and u is an integer from 0 to 6, $A^2$ is —NHCO—, —CONH—, —OCONH— or SCONH—, $A^3$ is $(CH_2)_r$, $O(CH_2)_r$, $NH(CH_2)_r$, $S(CH_2)_r$ or —(CHQ)—, wherein r is an integer from 1 to 6 and Q is a substituted or unsubstituted alkyl or aryl group, sp is a divalent spacer or a bond, and k is an integer from 5 to 100, and R is hydrogen; a ligand suitable for specific binding to a receptor; a marker molecule; or a catalytically active group; and m is at least 2, with the proviso that (1) in the compound at least one R is not hydrogen, (2) there are at least two K that are not a bond, and (3) X, B and m are so selected that an intermolecular association of the K in liquid phase by the formation of hydrogen bonds is possible, with formation of aggregates that present on the surface a plurality of R that are not hydrogen, and (4) the molar mass of the fragment $X(K)_m$ is less than 20,000.

In the compound of formula (I), $A^2$ may also be —CO—.

Further preferred embodiments are the subject of the subsidiary claims.

In a preferred embodiment, the molar mass of the fragment $X(K)_m$ is less than 10,000, preferably less than 4,000.

Self-association of compounds of the general formula (I) gives rise to aggregates that act as highly efficient multivalent inhibitors of biological recognition processes.

In the compounds of formula (I), X, B and m are so selected that an intermolecular association of the K in liquid phase is possible, especially under aqueous conditions, preferably under in vivo conditions, with formation of aggregates that present on the surface a plurality of R that are not hydrogen.

It has been found that by the formation of the aggregates according to the invention the disadvantages of the previously known multivalent active ingredients can be avoided.

It has been found especially that the slight increase in binding affinity in comparison with a monovalent active ingredient where a plurality of ligands are covalently bonded to a low molecular weight carrier or to a dendrimer is to be attributed to the fact that although such molecules do present a plurality of ligands, the latter cannot be arranged (or only some of them can be arranged) in such a manner that a thermodynamically advantageous interaction with receptors is achieved. It has been found that the interaction of a polyvalent active ingredient can be improved by dynamically coupling the ligand arrangement to the receptor arrangement. It has been found that this dynamic coupling can be achieved by way of an intermolecular aggregate formation in which special molecular regions of the active ingredient associate intermolecularly and thus an adaptation of the ligand arrangement is facilitated. Finally, it has been found that the adaptation of the ligand arrangement so facilitated results in a drastic increase in the binding affinity of the polyvalent active ingredient.

By virtue of the reversibility of the aggregate formation, the compounds of the present invention enable a molecular unit to interact polyvalently with a plurality of receptors, with subsequent optimisation of the ligand arrangement, there being found a thermodynamically advantageous arrangement without any undesirable side effects, such as the insertion of the compounds into the cell membrane.

The compounds of the present invention are small molecules, which would not be expected to have an action as antigen, and the other disadvantages that occur with polymeric polyvalent active ingredients are also avoided.

The molecular structure of the compounds of general formula (I) is substantially distinguished by three structural features:

an m-valent fragment X, a plurality of molecule chains K, which are covalently bonded to the fragment X, at least one terminal group R, which is a ligand suitable for specific binding to a receptor; a marker-molecule; or a catalytically active group.

The molecule chains K are distinguished by a chemical structure that allows an intermolecular association in liquid phase also under aqueous conditions, especially in vivo conditions, with formation of aggregates. The formation of the aggregates is based on non-covalent interactions, it being possible for the non-covalent interactions to be ionic interactions, van der Waals interactions, hydrophobic interactions or preferably hydrogen bonds. The structure of non-covalent bonds between a plurality of compounds of the general formula (I) brings about a self-association and thus the formation of aggregates.

The compounds of the general formula (I) have at least one terminal group R that is derived, for example, from a biologically active ligand or from a marker. The terminal groups R are covalently bonded to the terminal ends of the molecule chains serving for the association. The bonding of those groups can be effected directly or by way of a spacer. As spacer there can be used a divalent molecular fragment which does not participate in the intermolecular association brought about by non-covalent interactions, but which merely serves to hold the terminal groups R. Such a spacer is formally part of the molecule chain K.

According to the invention, K in the formula (I) may be $$A^1-(A^2-A^3)_k\text{-sp}$$

wherein $A^1$ is $(CH_2)_tY(CH_2)_u$, wherein

Y is >C=O, >NH, —O—, —S— or a bond, t is an integer from 0 to 6 and u is an integer from 0 to 6, $A^2$ is —NHCO—, —CONH—, —OCONH— or SCONH—, $A^3$ is $(CH_2)_r$, $O(CH_2)_r$, $NH(CH_2)_r$, $S(CH_2)_r$ or —(CHQ)—, wherein r is an integer from 1 to 6 and Q is a substituted or unsubstituted alkyl or aryl group, sp is a divalent spacer or a bond, and k is an integer from 5 to 100.

In the compound of formula (I), $A^2$ may also be —CO—.

Special preference is given to compounds of the general formula (I), wherein m is an integer from 2 to 4, and X is $CH_{4-m}$, $NH_{3-m}$, $N^+H_{4-m}$, >P– (when m=3), >P$^+$< (when m=4), >B– (when m=3), a linear atom group $C_2H_{6-m}$, >CH(CH$_2$)$_z$CH<, >C=C<, >N—N<, >N(CH$_2$)$_z$N< wherein z=2-6, when m=4), a carbocyclic atom group $C_6H_{6-m}$, $C_6H_{12-m}$, or a heterocyclic atom group $C_3N_3$ (when m=3), $C_4N_2$ (when m=4).

It is especially preferable for at least 3 K to be present in a compound of the general formula (I). Special preference is given to compounds of the general formula (I) in which at least two R, preferably three R, are not hydrogen.

When more than one terminal group R is present in a compound of the general formula (I), those groups may be identical or different.

As examples of the ligands suitable for specific binding to a receptor that function as terminal groups R of compounds of the general formula (I) there may be mentioned naturally occurring biological recognition structures, such as mono- or oligo-saccharides, peptides, mono- or oligo-nucleotides or nucleic bases. It is also possible, however, to use synthetic derivatives of those compounds or other organic or inorganic compounds that are recognised by biological receptors. As ligands there may also be used known compounds that are used in free form as therapeutic active ingredients. There may be mentioned by way of example:

anti-tumour agents, such as, for example, daunomycin, doxorubicin, vinblastine, bleomycin;
  antibiotics, such as, for example, penicillins, erythromycins, azidamfenicol, cefalotin and griseofulvin;
  antagonists of blood platelet activation factors;
  leucotriene antagonists;
  inhibitors of the cyclooxygenase system, such as, for example, salicylic acid compounds;
  lipoxygenase inhibitors;
  antiphlogistics, such as, for example, indometacin;
  antirheumatics, such as, for example, nifenazone;
  therapeutic radionuclides, such as, for example, bismuth;
  neuraminidase;
  inhibitors, such as, for example, zanamivir.

It is preferable to use oligosaccharides that are present on cell surfaces as constituents of glycoproteins, glycolipids or proteoglycans, and also any desired constituent parts thereof.

Special oligosaccharides that can be used as terminal group R are as follows: sialic acid, sialyl lactose, sialyl lactosamine, lactose, Galα1-3Gal, Galα1-3(Fucα1-2)Gal, GalNAcα1-3(Fucα1-2)Gal, Neu5Acα2-6GalNAc, SiaLe$^A$, SiaLe$^X$, HSO$_3$Le$^A$, HSO$_3$Le$^X$, Galα1-3Galβ1-4GlcNAc, Galα1-3Galβ1-4Glc, Neu5Acα2-6Galβ1-4GlcNAc.

In addition, preference is given to sialic acid benzyl glycoside, HSO$_3$GlcAβ1-3Gal, HSO$_3$GlcAβ1-3Galβ1-4GlcNAcβ1-3Galβ1-4-Glc, GalNacα, GalNAcα1-3(Fucα1-2)Galβ1-4GlcNAc, Galα1-3(Fucα1-2)Galβ1-4GlcNAc, HSO$_3$(Sia)Le$^X$, HSO$_3$(Sia)Le$^A$, Le$^Y$, GlcNAcβ1-6 (GlcNAcβ1-3)Galβ1-4Glc, GalNAcβ1-4(Neu5Acα2-3)Galβ1-4Glc, mannose-6-phosphate, GalNAcβ1-4GlcNAc, oligo-sialic acid, N-glycolylneuraminic acid, Galα1-4Galβ1-4Glc, Galα1-4Galβ1-4GlcNAc.

Derivatives or mimetics of the above-mentioned mono- or oligo-saccharides, peptides, mono- or oligo-nucleotides or nucleic bases can also be used.

The terminal groups R can also be derived from marker molecules. Such marker molecules enable compounds of the general formula (I) to be used in diagnostic applications. All marker molecules known to the person skilled in the art for in vitro diagnostic test systems, such as, for example, biotin, fluorescein, rhodamine, digoxigenin or radioactive markers, come into consideration for the purposes of the present invention. Special mention may be made of markers known to the person skilled in the art for in vivo diagnosis, such as radioactive markers that contain a bound radionuclide, e.g. technetium, X-ray contrast media that contain e.g. an iodised compound, or nuclear resonance contrast media, e.g. based on gadolinium compounds.

It is proposed that in a preferred embodiment the terminal groups R be so selected that aggregates are obtained which, on the one hand, interact with suitable receptors by way of suitable ligands through polyvalent interactions and, on the other hand, contain marker units. As a result, the polyvalent interactions are accessible to detection and the compounds can be used in a diagnostic procedure.

The aggregates can in this case be synthesised from compounds of formula (I) that contain both ligands and the marker radicals. Such an aggregate preferably comprises only one special compound of the general formula (I). On the other hand, however, an aggregate can also comprise a plurality of different compounds of formula (I), the compounds containing either ligands or marker radicals.

The present invention also provides an aggregate of the following general formula (II)

$$\{X(B)_m\}_n \qquad (II)$$

wherein
  $X(B)_m$ may be identical or different and denote a compound of the general formula (I), as defined in any one of claims 1 to 11, and
  n is from 2 to 100,000, and wherein $X(B)_m$ are non-covalently bonded.

The present invention provides especially an aggregate having a leaf-like structure and having linear, cyclic, polycyclic, polyhedral, spherical or dendritic structure. The aggregates may consist of two or more different compounds of the general formula (I).

The present invention also provides compounds of the general formula (III). The compounds of general formula (III) correspond to those of formula (II) wherein all terminal groups R are hydrogen atoms. Such compounds can be used with the compounds of the general formula (I) described above in order to alter the properties of the aggregates.

The present invention provides especially a compound of the general formula (III)

$$X(B)_m \qquad (III)$$

wherein
X is an m-valent unit and
B are identical or different and denote K-H, wherein
  K is $A^1$—$(A^2$—$A^3)_k$-sp, wherein
    $A^1$ is $(CH_2)_t Y(CH_2)_u$, wherein
      Y is >C=O, >NH, —O—, —S— or a bond,
      t is an integer from 0 to 6 and
      u is an integer from 0 to 6,
    $A^2$ is —NHCO—, —CONH—, —OCONH— or SCONH—,
    $A^3$ is $(CH_2)_r$, $O(CH_2)_r$, $NH(CH_2)_r$, $S(CH_2)_r$ or —(CHQ)—, wherein
      r is an integer from 1 to 6 and
      Q is a substituted or unsubstituted alkyl or aryl group,
    sp is a divalent spacer or a bond, and
    k is an integer from 5 to 100, and
m is at least 2, with the proviso that (1) X, B and m are so selected that an intermolecular association of the K in liquid phase is possible, especially under aqueous conditions, by the formation of hydrogen bonds, with formation of aggregates, and
(2) the molar mass of the fragment $X(K)_m$ is less than 20,000, especially less than 4000.

In the compound of formula (II), $A^2$ may also be —CO—.

In a preferred embodiment, K in formula (III) is $$A^1\text{—}(A^2\text{—}A^3)_k\text{-sp}$$

wherein
$A^1$ is $(CH_2)_tY(CH_2)_u$, wherein
  Y is >C=O, >NH, —O—, —S— or a bond,
  t is an integer from 0 to 6 and
  u is an integer from 0 to 6,
$A^2$ is —NHCO—, —CONH—, —OCONH— or SCONH—,
$A^3$ is $(CH_2)_r$, $O(CH_2)_r$, $NH(CH_2)_r$, $S(CH_2)_r$ or —(CHQ)—, wherein
  r is an integer from 1 to 6 and
  Q is a substituted or unsubstituted alkyl or aryl group,
sp is a divalent spacer or a bond, and
k is an integer from 5 to 100.

The preparation of the compounds of the general formula (I) will now be described. The compounds of formula (III) can also be prepared in accordance with this preparation method.

The synthesis of the compounds of the general formula (I) is advantageously carried out in each case starting from the corresponding tetramines by successive chain lengthening (Scheme 1), in which procedure known methods of peptide chemistry are used, the Boc group being used as N-protecting group. The amide bonds are preferably formed using the active ester method.

Scheme 1

$[H_2NCH_2\text{—}]_4C \longrightarrow [BocNH(CH_2)_pCONHCH_2\text{—}]_4C \longrightarrow$
$[H_2N(CH_2)_pCONHCH_2\text{—}]_4C \longrightarrow \longrightarrow$
$[H\text{—}AC_mGly_nNHCH_2\text{—}]_4C$ p = 1 or 6, n = 0 to 7, m = 0 to 3

The terminal groups are advantageously linked likewise by way of the active ester method to the compounds of the general formula (I) synthesised according to Scheme 1 (Scheme 2).

Scheme 2

$[H\text{—}AC_mGly_nNHCH_2\text{—}]_4C\ +$
$\quad Sug\text{-}sp\text{-}AC_m\text{-}Ad\text{-}ONp \longrightarrow \longrightarrow$
$\quad [Sug\text{-}sp\text{-}AC_m\text{-}Ad\text{-}AC_mGly_nNHCH_2\text{—}]_4C$ Sug-sp =
Neu5Acα2-OCH$_2$(p-C$_6$H$_4$)NHCOCH$_2$NH——  (Neu5Ac-Gab-)
Neu5Acα2-O(CH$_2$)$_3$NH——  (Neu5Ac-Ap-)
Neu5Acα2-3Galβ1-4Glcβ1-NHCOCH$_2$NH——  (3'SL-NHSCOCH$_2$NH$_2$——)
Galα1-3Galβ1-O(CH$_2$)$_3$NH——  (B$_{dt}$-Ap-)

The formation of aggregates will now be described in detail and with reference to the Figures.

Scheme 3

$X[A^1\text{—}(A^2-A^3)_k\text{—sp-R}]_m \rightleftharpoons \{X[A^1\text{—}(A^2-A^3)_k\text{—sp-R}]_m\}_n$ That intermolecular association takes place spontaneously and results in the formation of stable and ordered structures. The course of that process depends upon the molecular structure of the compounds of the general formula (I) used and upon the external conditions. The molar masses, sizes and shapes of the aggregates formed are likewise determined by those factors.

The non-covalent nature of the bonds between the compounds of the general formula (I) gives rise to the reversibility of the aggregate formation and, in the event of a change in the external conditions, allows dissociation of the aggregates to form compounds of the general formula (I) or conversion thereof into other aggregates, in each case with a view to forming the most thermodynamically stable structures.

The self-association of compounds of the general formula (I) to form aggregates can be observed both in solution and on surfaces.

By means of scanning tunnel microscopy (STM) and atomic force microscopy it has been shown that the aggregate {[Neu5Ac-Gab-Ad-Gly$_7$-NHCH$_2$-]$_4$C}$_x$ forms ordered chain structures on a graphite substrate.

The formation of aggregates in solution can be observed by light scattering experiments or by gel permeation chromatography.

Figure 1:
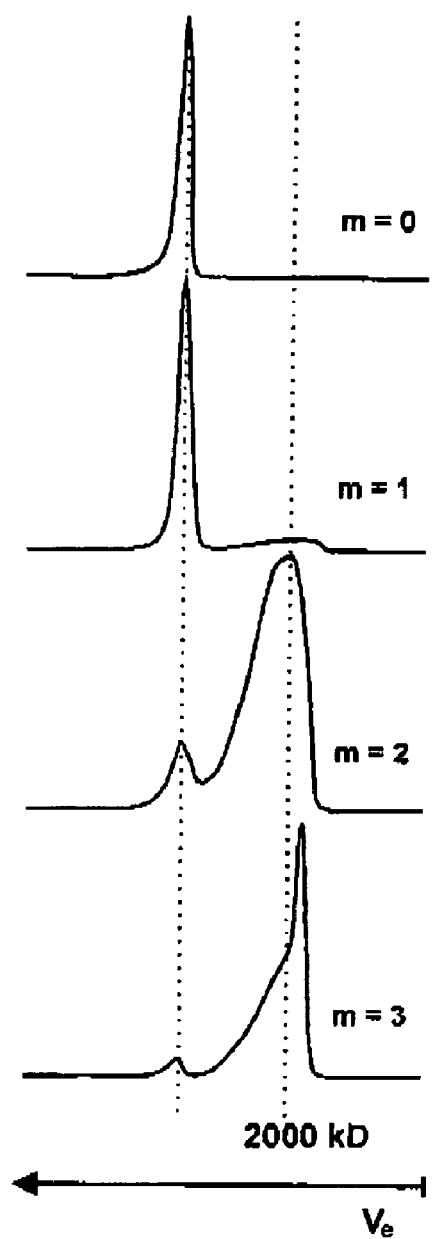
FIG. 1 shows elution profiles of aggregates {[Neu5Ac-Gab-Ac$_m$-Ad-Gly$_5$-NHCH$_2$-]$_4$C}$_x$, HPLC, TSK-4000, 0.2M NaCl.

The compound of the general formula (I) Neu5Ac-Gab-AC$_m$-Ad-Gly$_5$-NHCH$_2$-]$_4$C (m=1-3) associates at room temperature in aqueous and organic solvents. Investigation into the associates formed in water using gel permeation chromatography showed the formation of aggregates having molecular weights of about 2000 kD, as shown in FIG. 1.

Figure 2:
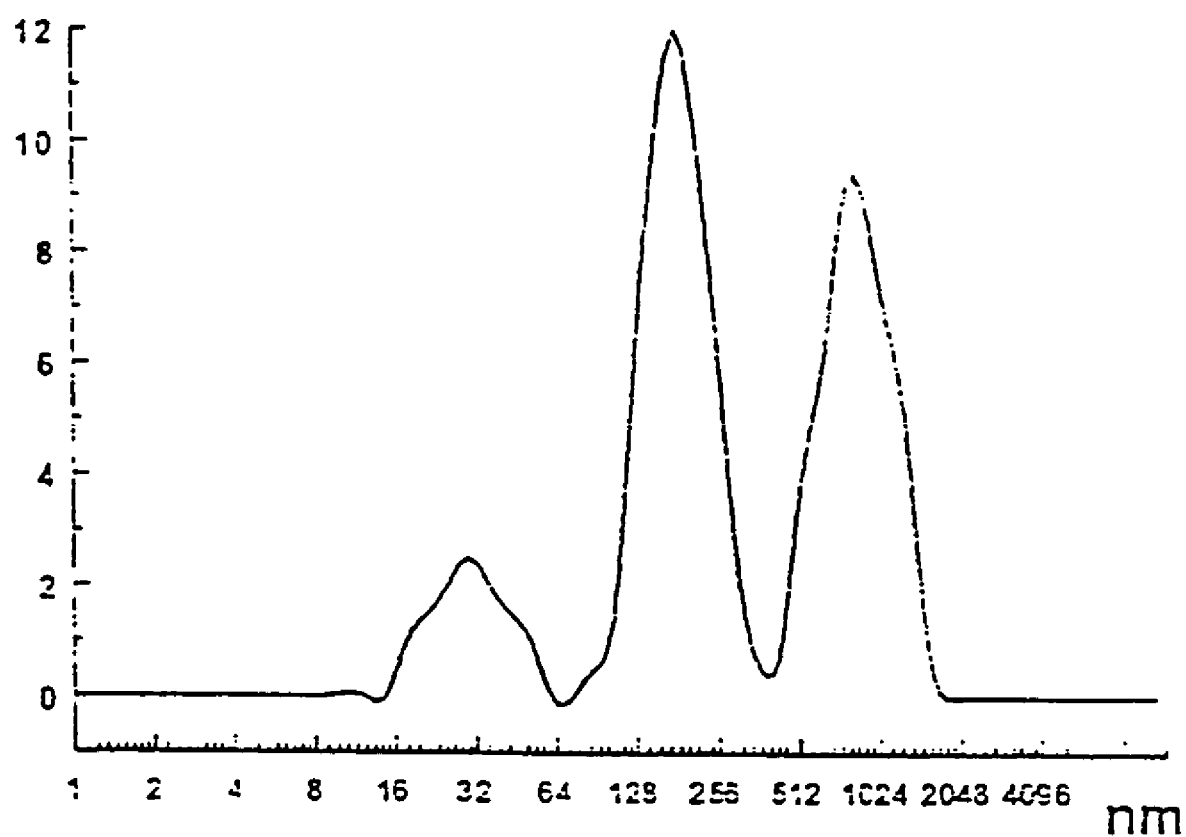
FIG. 2 shows the relative particle size distribution of aggregate {[Neu5Ac-Gab-Ad-AC$_3$-Gly$_5$-NHCH$_2$-]$_4$C}$_x$, 20° C. H$_2$O.
Figure 3:
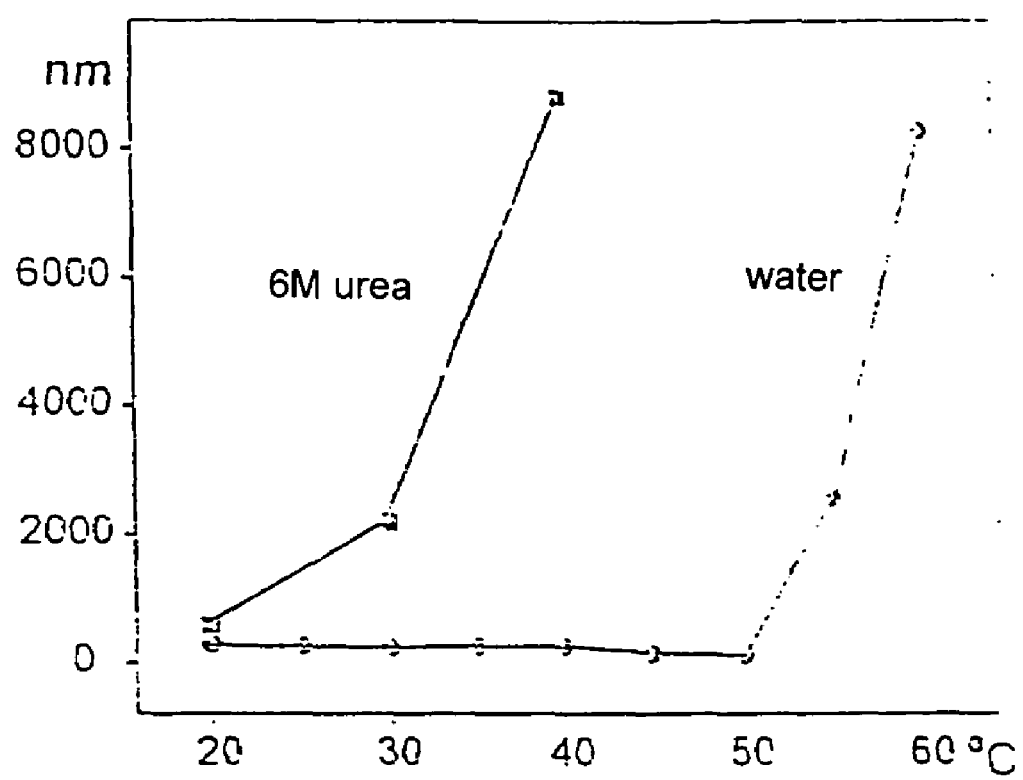
FIG. 3 shows the influence of temperature and of the presence of urea on the particle size of aggregate {[Neu5Ac-Gab-Ad-Gly$_7$-NHCH$_2$-]$_4$C}$_x$ The aggregates are high molecular weight non-covalent polymers that are formed by self-association of compounds of the general formula (I) (Scheme 3).

Investigation into the association of the compound of the general formula (I) [Neu5Ac-Gab-Ad-AC$_3$-Gly$_5$-NHCH$_2$-]$_4$C in water at 20° C. showed the formation of three types of aggregates having particle sizes between 25 and 2000 nm (FIG. 2). When the sample was heated to 60° C., a reduction in the relative proportion of the smaller particles was observed, while at the same time the relative proportion of the larger particles increased and the total number of particles decreased. An increase in aggregate size with temperature was also observed in the case of the compound of the general formula (I) (48). That compound forms in water at 60° C. particles having sizes of up to 8000 nm (FIG. 3).

External conditions that determine the formation of the aggregates and the course of the intermolecular association include, in addition to temperature, the pH value and the nature and composition of the solvent. By means of light scattering experiments it has been shown that the compound [HCl.H-Gly$_7$-NHCH$_2$-]$_4$C (22a) in water at 20° C. is present in non-associated form, but by the addition of a 0.8M NaHCO$_3$ solution a self-association of the compound is achieved. The addition of HCl then enables the association to be reversed again (cf. Example 9).

The formation of aggregates is also influenced by the presence of components that are able to enter into interactions with the compounds of the general formula (I). Those components may be organic molecules, such as, for example, compounds of the formula (III), urea (FIG. 3), trifluoroethanol, methanol, acetone or other organic solvents. There may also be other compounds of the general formula (I) or (III) that on their own—under the given conditions—do not form associates.

In the case of compounds of the general formula (I) and aggregates, the process of self-association is influenced also by the interactions between the ligands and the corresponding receptors. That influence may, for example, be such that only as a result of the presence of the receptors is an association of compounds of the general formula (I) brought about, more specifically under conditions in which association of those compounds would not otherwise take place. As a result of the reversibility of the aggregate formation it is equally possible that aggregates, in the presence of receptors, change in such a manner, with rearrangement or modification of the composition, that a thermodynamically advantageous state of the entire system consisting of aggregate and receptor is achieved. The aggregates can therefore adapt themselves to different receptor arrangements and thus optimise an interaction between the receptors and ligands. That optimisation by subsequent adaptation of the polyvalent interactions constitutes a substantial advantage over the prior art.

Special biologically active aggregates will now be described. As a result of the self-association of compounds of the general formula (I) with biologically active ligands there are formed biologically active aggregates that act as highly effective multivalent inhibitors of biological recognition processes. The specific activity of such an inhibitor is dependent upon the affinity of terminal groups R, and also upon the "matrix" of the aggregate, that is to say the structure of the compound of the general formula (I) used as carrier.

Tables 2 and 3 show the influence of the matrix structure on the inhibition of the viral cell adhesion of influenza viruses, measured in a fetuin binding assay known to the person skilled in the art. That assay reveals an increase in the specific activity of the inhibitor by more than three orders of magnitude in comparison with the activity of the free ligand Neu5Acα-Bn in the case of the aggregate {[Neu5Ac-Gab-Ad-AC$_3$-Gly$_5$-NHCH$_2$-]$_4$C}$_x$ (44).

TABLE 1

Inhibition of viral cell adhesion of influenza viruses, strain A/NIB/44/90M H3N2, FBI test, Neu5AcαBn as a reference compound, specific activity per Neu5Ac group

| Inhibitor | Relative activity |
|---|---|
| Neu5Acα-OBn | 1 |
| [Neu5Ac-Gab-Ad-Gly$_n$-NHCH$_2$-]$_4$C (n = 0-5) | 2 |
| [Neu5Ac-Ap-Ad-Gly$_n$-NHCH$_2$-]$_4$C (n = 3-5) | 1 |
| [Neu5Ac-Gab-Ad-GlyGluGly-NHCH$_2$-]$_4$C | 5 |
| [Neu5Ac-Gab-AC-Ad-Gly$_5$-NHCH$_2$-]$_4$C | 15 |
| [Neu5Ac-Gab-AC$_2$-Ad-Gly$_5$-NHCH$_2$-]$_4$C | 330 |
| [Neu5Ac-Gab-AC$_3$-Ad-Gly$_5$-NHCH$_2$-]$_4$C | 1000 |
| [Neu5Ac-Gab-Ad-AC$_2$-Gly$_5$-NHCH$_2$-]$_4$C | 1000 |
| [Neu5Ac-Gab-Ad-AC$_3$-Gly$_5$-NHCH$_2$-]$_4$C | 2500 |

TABLE 2

Inhibition of viral cell adhesion of influenza viruses inhibition of strain A/Duck/Alberta/60/67 H12N5, FBI test, 3'SL as a reference compound, specific activity per 3'SL group

| Inhibitor | Relative activity |
|---|---|
| 3'SL | 1 |
| [3'SL-NHCOCH$_2$NH-Ad-Gly$_5$-NHCH$_2$-]$_4$C | 20 |
| [3'SL-NHCOCH$_2$NH-Ad-Gly$_7$-NHCH$_2$-]$_4$C | 200 |

A further example of the increase in biological activity of a biological ligand resulting from its binding to an aggregate is the compound {[B$_{di}$-Ap-Ad-AC$_3$-Gly$_5$-NHCH$_2$-]$_4$C}$_x$ (49) as inhibitor of the cytotoxicity of human blood sera with respect to porcine kidney cells PK15. The aggregate (49) exhibits a specific activity three orders of magnitude higher than the free ligand Galα1-3Gal (B disaccharide).

Abbreviations used:
Np para-nitrophenyl
NOS N-oxysuccinimidyl
Boc tert-butyloxycarbonyl
AC 6-aminocaproyl
Ad 1,6-hexanedioyl
Ap 3-aminopropyl
Gab 4-(glycylamido)-benzyl
Sug carbohydrate radical
SL sialyl lactose
Bn benzyl
LC column chromatography
TLC thin-layer chromatography The invention will now be described in greater detail with reference to Examples.

Materials and Methods:

$^1$H NMR spectra (δ, ppm, TMS) were recorded using a spectrometer of the WM-500 type from Bruker (USA) at 303° K.

Mass spectra were recorded using a time-of-flight spectrometer of the MSBCh type (Sumy, Ukraine) (ionisation by cleavage products of californium-252 at an acceleration voltage of +15 eV).

The light scattering experiments were carried out using the following apparatus: Coultronics Coulter N4-MD (He-Ne laser, λ=632.8 nm, measurement of the scattering at an angle of 62.5° to the incident light beam), Spectra-Physics 164 (argon laser, λ=528.7 nm and λ=611.5 nm, measurement of the scattering at an angle of 90° to the incident light beam).

Silica gel 60 (40-63 μm) (Merck) was used for column chromatography. Sephadex of types LH-20, G-10, G-25 (Pharmacia, Sweden) and TSK-4000 (HPLC) were used for gel permeation chromatography.

For TLC, silica gel 60 (Merck) and silica gel 60 glass plates with fluorescent indicator F254 (Merck) were used. For the detection of spots on the TLC plates, the following methods were used:

heating after spraying with a 7% H$_3$PO$_4$ solution (carbohydrate compounds);

heating after spraying with a 2% ninhydrin solution in ethanol (compounds having primary amino groups);

heating after a dwell time of 10 minutes in a chamber over conc. HCl and subsequent spraying with a 2% ninhydrin solution in ethanol (compounds having Boc-protected amino groups);

dwell time of 10 minutes in a chamber over conc. NH$_3$ (4-nitrophenyl ester);

observing the plates under UV.

For TLC, the following eluant systems were used:
A—toluene/ethyl acetate 2:1
B—acetone/ethyl acetate/methanol 10:4:1
C—CHCl$_3$/MeOH 7:1
D—CHCl$_3$/ethyl acetate/MeOH/AcOH 9:3:2:0.2
E—iPrOH/ethyl acetate/H$_2$O 2:3:1
F—EtOH/NH$_{3(aq)}$ 2:1
G—iPrOH/ethyl acetate/H$_2$O 4:3:2
H—iPrOH/acetone/H$_2$O 4:3:2

Preparation of Known Starting Compounds

Tetrakis(aminomethyl)methane tetrahydrochloride (1) was prepared analogously to the literature (E. B. Fleischer, A. E. Gebala, A. Levey, P. A. Tasker, *J. Org. Chem.*, 36, 3042, 1971)

TLC: R$_f$=0.6; eluant—25% ammonia/water; developer—ninhydrin.

M.p. >300° C. $^1$H-NMR spectrum in D$_2$O (δ, ppm): 3.45 (s, CH$_2$).

4-Nitrophenyl trifluoroacetate (2) was prepared analogously to the literature (S. Sakakibara, N. Inukai, *Bull. Chem. Soc. Jap.*, 37, 1231, 1964).

Di-(4-nitrophenyl) adipate (3) was prepared analogously to the literature (S. Sakakibara, N. Inukai, *Bull. Chem. Soc. Jap.*, 37, 1231, 1964).

R$_f$=0.76, eluant D A.

$^1$H-NMR spectrum in CDCl$_3$ (δ, ppm): 1.871 (m, 4H, 2 COCH$_2$C$\underline{H}_2$), 2.666 (m, 4H, 2 COC$\underline{H}_2$), 7.255 and 8.240 (m, 8H, J$_{2,3}$ 9 Hz, Ar).

Methyl [4-(tert-butyloxycarbonyl-glycilamido)benzyl 5-acetamido-4,7,8,8-tetra-O-acetyl-3,5-didesoxy-α-D-glycero-D-galacto-nonulopyranosid]oate Ac$_4$(OMe)Neu5Ac-Gab-Boc (4) was prepared analogously to the literature (U.S. Pat. No. 5,571,836, 1996).

$^1$H-NMR spectrum (CDCl$_3$, δ, ppm): 1.448 (s, 9H, CMe$_3$), 1.849, 1.994, 2.008, 2.111, 2.127 (s, 5×3H, 5 Ac), 1.979 (dd, 1H, H-3$_{ax}$ Neu5Ac), 2.613 (dd, 1H, J$_4$ 4.6 Hz, J$_{3ax}$ 12.9 Hz, H-3$_{eq}$ Neu5Ac), 3.637 (s, 3H, COOCH$_3$), 3.882 (d, 2H, J 6 Hz, COC$\underline{H}_2$NH), 4.058 (ddd, 1H, H-5 Neu5Ac), 4.074 (dd, 1H, J$_{9b}$ 12.5 Hz, J$_8$ 5.9 Hz, H-9a Neu5Ac), 4.112 (dd, 1H, J$_5$ 10.6, J$_7$ 2.3 Hz, H-6 Neu5Ac), 4.299 (dd, 1H, J$_{9b}$ 12.5 Hz, J$_8$ 2.7 Hz, H-9b Neu5Ac), 4.366 and 4.735 (d, 2×1H, J 12 Hz, OC$\underline{H}_2$Ar), 4.847 (ddd, 1H, J$_5$ 10 Hz, J$_{3ax}$ 12.3 Hz, J$_{3eq}$ 4.6 Hz, H-4 Neu5Ac), 5.24 (br., 1H, N$\underline{H}$Boc), 5.251 (d, 1H, J$_5$ 9.8 Hz, NH), 5.314 (dd, 1H, J$_6$ 2.3 Hz, J$_8$ 8.2 Hz, H-7 Neu5Ac), 5.424 (ddd, 1H, H-8 Neu5Ac), 7.258 and 7.445 (d, 2×2H, J 8.4 Hz, Ar), 8.144 (br. s, 1H, N$\underline{H}$Ar).

Neu5Acα2-3Galβ1-4Glcβ-NHCOCH$_2$NH$_2$ (12) was prepared analogously to the literature (L. M. Likhosherstov, O. S. Novikova, V. A. Derevitskaja, N. K. Kochetkov, *Carbohydrate Research*, 146, C1-C5, 1986; and I. D. Manger, T. W. Rademacher, R. A. Dwek, *Biochemistry*, 31, 10724, 1992).

$^1$H-NMR spectrum (D$_2$O, δ, ppm): 1.82 (dd, 1H, H-3$_{ax}$ Neu5Ac, J$_4$ 12 Hz), 2.06 (s, 3H, NAc), 2.79 (dd, 1H, H-3$_{eq}$ Neu5Ac, J$_{3ax}$ 12.4 Hz, J$_4$ 4.6 Hz), 3.48 (m, 1H, H-2 Glc, J$_3$ 9 Hz), 3.61 (dd, 1H, H-2 Gal), 3.99 (dd, 1H, H-4 Gal), 4.14 (dd, 1H, H-3 Gal, J$_2$ 9.8 Hz, J$_4$ 3.1 Hz), 4.57 (d, 1H, H-1 Gal, J$_2$ 7.8 Hz), 5.09 (d, 1H, H-1 Glc, J$_2$ 9.3 Hz).

Galα1-3Galβ-O(CH$_2$)$_3$NH$_2$ (13) was prepared analogously to the literature (E. Yu. Korchagina, N. V. Bovin, *Bioorganicheskaya Khimiya*, 1992, 18, 283, Rus).

The compounds BocGlyNOS, BocGlyGlyNOS and BocAC-ONp were prepared using N,N'-dicyclohexylcarbodiimide analogously to the literature (G. W. Anderson, J. E. Zimmerman, F. M. Callahan, *J. Amer. Chem. Soc.*, 86, 1839, 1964; M. Bodanszky, V. du Vigneaud, *J. Amer. Chem. Soc.*, 81, 5688, 1959).

EXAMPLE 1

Preparation of Ac$_4$(OMe)Neu5Ac-Gab-AC-Boc (5)

10 ml of CHCl$_3$ and 2 ml of CF$_3$COOH were added to 0.5 mmol of compound (4). The reaction mixture was stirred at room temperature for one hour; 2 ml of toluene were added and the mixture was concentrated by evaporation in vacuo and dried. The residue was dissolved in 10 ml of CHCl$_3$, and 1.5 mmol of 6-N-Boc-amino-(4-nitrophenyl) hexanoate and 0.3 ml of NEt$_3$ were added. The reaction mixture was stirred at room temperature for 24 hours and concentrated by evaporation in vacuo. The resulting residue was chromatographed over silica gel.

The compounds Ac$_4$(OMe)Neu5Ac-Gab-AC$_2$-Boc (6) and Ac$_4$(OMe)Neu5Ac-Gab-AC$_3$-Boc (7) were prepared in an analogous manner (see Table 4).

TABLE 3

(Example 1)

| Product | Starting compound | TLC: eluant A, R$_1$ | Column chromatography | Yield, % |
|---|---|---|---|---|
| Ac$_4$(OMe)Neu-5Ac-Gab-AC-Boc (5) | (4) | 0.6 | CHCl$_3$/MeOH 35:1 → 10:1 | 90 |
| Ac$_4$(OMe)Neu-5Ac-Gab-AC$_2$-Boc (6) | (5) | 0.45 | acetone/ethyl acetate/MeOH 10:4:0.5 → 10:4:3 | 72 |
| Ac$_4$(OMe)Neu-5Ac-Gab-AC$_3$-Boc (7) | (6) | 0.25 | acetone/ethyl acetate/MeOH 10:4:1 → 10:4:5 | 70 |

$^1$H-NMR spectra (CDCl$_3$, δ, ppm):

Ac$_4$(OMe)Neu5Ac-Gab-AC-Boc (5): 1.331, 1.468, 1.655 (m, 3CH$_2$), 1.402 (s, 9H, CMe$_3$), 2.264 (t, 2H, J 7.5 Hz, C$\underline{H}_2$CONHCH$_2$CO), 3.066 (m~quadr, 2H, J 6.6 Hz, C$\underline{H}_2$NHBoc), 4.060 (d, 2H, J 5 Hz, COC$\underline{H}_2$NH), 4.364 and 4.733 (d, 2×1H, J 12 Hz, OC$\underline{H}_2$Ar), 4.571 (br., 1H, N$\underline{H}$Boc), 6.521 (br., 1H, COCH$_2$N$\underline{H}$CO), 7.253 and 7.460 (d, 2×2H, J 8.4 Hz, Ar), 8.547 (br. s, 1H, N$\underline{H}$Ar). Neu5Acα fragment: (see (4)).

Ac$_4$(OMe)Neu5Ac-Gab-AC$_2$-Boc (6): 1.280, 1.338, 1.447, 1.482, 1.582, 1.655, 2.107 (m, 7CH$_2$), 1.403 (s, 9H, CMe$_3$), 2.276 (t, 2H, J 7.2 Hz, C$\underline{H}_2$CONHCH$_2$CO), 3.060 (m~quadr, 2H, J 6.6 Hz, C$\underline{H}_2$NHBoc), 3.216 (m~quadr, 2H, J 6.4 Hz, C$\underline{H}_2$NH), 4.040 (d, 2H, J 5 Hz, COC$\underline{H}_2$NH), 4.353 and 4.728 (d, 2×1H, J 12 Hz, OC$\underline{H}_2$Ar), 4.651 (br., 1H, N$\underline{H}$Boc), 5.793 (t, 1H, J 5 Hz, CH$_2$N$\underline{H}$CO), 6.714 (br., 1H, COCH$_2$N$\underline{H}$CO), 7.245 and 7.467 (d, 2×2H, J 8.4 Hz, Ar), 8.666 (br. s, 1H, N$\underline{H}$Ar). Neu5Acα fragment: (see (4)).

Ac$_4$(OMe)Neu5Ac-Gab-AC$_3$-Boc (7): 1.283, 1.336, 1.447, 1.482, 1.594, 1.655, 2.117 (m, 11CH$_2$), 1.401 (s, 9H, CMe$_3$), 2.282 (t, 2H, J 7.2 Hz, C$\underline{H}_2$CONHCH$_2$CO), 3.045 (m~quadr, 2H, J 6.6 Hz, C$\underline{H}_2$NHBoc), 3.214 (m~quadr, 4H, J 6.4 Hz, C$\underline{H}_2$NH), 4.040 (d, 2H, J 5 Hz, COC$\underline{H}_2$NH), 4.353 and 4.728 (d, 2×1H, J 12 Hz, OC$\underline{H}_2$Ar), 4.669 (br., 1H, N$\underline{H}$Boc), 5.876 (t, 1H, J 5.5 Hz, CH$_2$N$\underline{H}$CO), 6.071 (br., 1H, CH$_2$N$\underline{H}$CO), 6.940 (br., 1H, COCH$_2$N$\underline{H}$CO), 7.242 and 7.483 (d, 2×2H, J 8.4 Hz, Ar), 9.033 (br. s, 1H, NHAr). Neu5Acα fragment: (see (4)).

EXAMPLE 2

Preparation of Ac$_4$(OMe)Neu5Ac-Gab-AC-Ad-ONp (9)

10 ml of CHCl$_3$ and 2 ml of CF$_3$COOH were added to 0.5 mmol of compound (5). The reaction mixture was stirred at room temperature for one hour; 5 ml of toluene were added and the mixture was concentrated by evaporation in vacuo and dried. The residue was dissolved in 15 ml of tetrahydrofuran; 5 mmol of compound (3) and 0.3 ml of NEt$_3$ were added and the reaction mixture was stirred at room temperature for 24 hours. The excess NEt$_3$ was neutralised with CH$_3$COOH and the reaction mixture was concentrated by evaporation. The residue was dissolved in CHCl$_3$ and the resulting solution was washed with water and concentrated by evaporation. The resulting mixture was chromatographed over a column of silica gel (see Table 4).

The compounds Ac$_4$(OMe)Neu5Ac-Gab-Ad-ONp (8), Ac$_4$(OMe)Neu5Ac-Gab-AC$_2$-Ad-ONp (10) and Ac$_4$(OMe)Neu5Ac-Gab-AC$_3$-Ad-ONp (11) were prepared in an analogous manner (see Table 4).

TABLE 4

(Example 2)

| Product | Starting compound | TLC: eluant C, R$_f$ | Column chromatography | Yield, % |
|---|---|---|---|---|
| Ac$_4$(OMe)Neu-5Ac-Gab-Ad-ONp (8) | (4) | 0.6 | CHCl$_3$/i-PrOH 20:1 | 78 |
| Ac$_4$(OMe)Neu-5Ac-Gab-AC-Ad-ONp (9) | (5) | 0.55 | CHCl$_3$/MeOH/AcOH 35:1:02 → 15:1:0.2 | 65 |
| Ac$_4$(OMe)Neu-5Ac-Gab-AC$_2$-Ad-ONp (10) | (6) | 0.48 | CHCl$_3$/MeOH/AcOH 35:1:02 → 15:1:0.2 | 60 |
| Ac$_4$(OMe)Neu-5Ac-Gab-AC$_3$-Ad-ONp (11) | (7) | 0.43 | CHCl$_3$/MeOH/AcOH 35:1:02 → 15:1:0.2 | 62 |

$^1$H-NMR-spectra:

Ac$_4$(OMe)Neu5Ac-Gab-Ad-ONp (8) (CDCl$_3$, δ, ppm): 1.774 (m, 2H, CH$_2$CH$_2$COO), 1.843, 1.984, 2.00, 2.100, 2.117 (s, 5×3H, 5 Ac), 1.966 (dd, 1H, H-3$_{ax}$ Neu5Ac), 2.335 and 2.393 (m, 2×1H, CH$_2$CH$_2$CONH), 2.601 (t, 2H, J 6 Hz, CH$_2$CH$_2$COO), 2.604 (dd, 1H, H-3$_{eq}$ Neu5Ac), 3.645 (s, 3H, COOCH$_3$), 3.688 (t, 2H, J 4.7 Hz, CH$_2$CHhd 2CONH), 4.049 (ddd, 1H, H-5 Neu5Ac), 4.062 (dd, 1H, J$_8$ 6 Hz, H-9a, Neu5Ac), 4.074 (d, 2H, J$_{NH}$ 5.5 Hz, COCH$_2$NHCO), 4.111 (dd, 1H, J$_5$ 10.7, J$_7$ 2.3 Hz, H-6 Neu5Ac), 4.298 (dd, 1H, J$_{9b}$ 12.5 Hz, J$_8$ 2.9 Hz, H-9B, Neu5Ac), 4.343 and 4.722 (d, 2×1H, J 12 Hz, OCH$_2$Ar), 4.839 (ddd, 1H, J$_5$ 10.2 Hz, J$_{3ax}$ 12.3 Hz, J$_{3eq}$ 4.6 Hz, H-4 Neu5Ac), 5.307 (dd, 1H, J$_8$ 8.4 Hz, J$_6$ 2.3 Hz, H-7 Neu5Ac), 5.359 (d, 1H, J$_5$ 9.7 Hz, NH), 5.406 (ddd, 1H, H-8 Neu5Ac), 6.616 (t, 1H, COCH$_2$NHCO), 7.243 and 7.450 (d, 2×2H, J 8.5 Hz, p-C$_6$H$_4$NH), 7.221 and 8.208 (d, 2×2H, J 9 Hz, p-C$_6$H$_4$NO$_2$), 8.586 (s, 1H, NHAr).

Ac$_4$(OMe)Neu5Ac-Gab-AC-Ad-ONp (9) (CDCl$_3$, δ, ppm): 1.341 (m, 2H, COCH$_2$CH$_2$CH$_2$CH$_2$NH), 1.495 and 1.666 (m, 2×2H, COCH$_2$CH$_2$CH$_2$CH$_2$NH), 1.729 (m, 2H, CH$_2$COO), 1.856, 1.991, 2.010, 2.110 and 2.129 (s, 5×3H, 5 Ac), 1.976 (dd, 1H, H-3$_{ax}$ Neu5Ac), 2.138, 2.175 (m, 2×1H, CH$_2$CH$_2$CONH), 2.182 and 2.267 (t, 2×2H, 2 CH$_2$CONH), 2.601 (~t, 2H, J 6.8 Hz, CH$_2$CHhd 2COO), 2.611 (dd, 1H, J$_{3ax}$ 12.8, J$_4$ 4.5 Hz, H-3$_{eq}$ Neu5Ac), 3.228 (m~quadr, 2H, J 6.6 Hz, CH$_2$NHCO), 3.645 (s, 3H, COOCH$_3$), 4.022 (d, 2H, J$_{NH}$ 5.4 Hz, COCH$_2$NHCO), 4.050 (ddd, 1H, H-5 Neu5Ac), 4.065 (dd, 1H, J$_8$ 6 Hz, H-9a Neu5Ac), 4.113 (dd, 1H, J$_5$ 10.8, J$_7$ 2.3 Hz, H-6 Neu5Ac), 4.295 (dd, 1H, J$_{9a}$ 12.5 Hz, J$_8$ 2.9 Hz, H-9b Neu5Ac), 4.357 and 4.732 (d, 2×1H, J 12 Hz, OCH$_2$Ar), 4.848 (ddd, 1H, J$_5$ 10 Hz, J$_{3ax}$ 12.2 Hz, J$_{3eq}$ 4.5 Hz, H-4 Neu5Ac), 5.170 (d, 1H, J$_5$ 10 Hz, NH), 5.308 (dd, 1H, J$_8$ 8.6 Hz, J$_6$ 2.3 Hz, H-7 Neu5Ac), 5.413 (ddd, 1H, H-8 Neu5Ac), 5.708 (t, 1H, CH$_2$CH$_2$NHCO), 6.483 (t, 1H, COCH$_2$NHCO), 7.251 and 7.427 (d, 2×2H, J 8.7 Hz, p-C$_6$H$_4$NH), 7.243 and 8.224 (d, 2×2H, J 9 Hz, p-C$_6$H$_4$NO$_2$), 8.298 (s, 1H, NHAr).

Ac$_4$(OMe)Neu5Ac-Gab-AC$_2$-Ad-ONp (10) (D$_6$-DMSO, δ, ppm): 1.231, 1.376, 1.485 and 1.608 (m, CH$_2$), 1.757 (dd, 1H, H-3$_{ax}$ Neu5Ac), 1.678, 1.917, 1.974, 2.023 and 2.092 (s, 5×3H, 5 Ac), 2.570 (dd, 1H, J$_{3ax}$ 12.4, J$_4$ 4.5 Hz, H-3$_{eq}$ Neu5Ac), 2.638 (t, 2H, J 7 Hz, CH$_2$CH$_2$COO), 3.009 (m, 4H, 2CH$_2$NHCO), 3.699 (s, 3H, COOCH$_3$), 3.859 (d, 2H, J$_{NH}$ 5.9 Hz, COCH$_2$NHCO), 3.904 (ddd, 1H, H-5 Neu5Ac), 4.027 (dd, 1H, J$_8$ 6.2 Hz, H-9a Neu5Ac), 4.089 (dd, 1H, J$_5$ 10.8, J$_7$ 2.6 Hz, H-6 Neu5Ac), 4.235 (dd, 1H, J$_{9a}$ 12.4 Hz, J$_8$ 3.1 Hz, H-9b Neu5Ac), 4.322 and 4.645 (d, 2×1H, J 11.7 Hz, OCH$_2$Ar), 4.715 (ddd, 1H, J$_5$ 10 Hz, J$_{3ax}$ 12 Hz, J$_{3eq}$ 4.5 Hz, H-4 Neu5Ac), 5.193 (dd, 1H, J$_8$ 8.4 Hz, J$_6$ 2. Hz, H-7 Neu5Ac), 5.341 (ddd, 1H, H-8 Neu5Ac), 7.216 and 7.554 (d, 2×2H, J 8.4 Hz, p-C$_6$H$_4$NH), 7.433 and 8.296 (d, 2×2H, J 9.2 Hz, p-C$_6$H$_4$NO$_2$), 7.674 (t, 1H, J 5.5 Hz, CH$_2$CH$_2$NHCO), 7.706 (d, 1H, J$_5$ 9.8 Hz, NH), 7.754 (t, 1H, J 5.8 Hz, CH$_2$CH$_2$NHCO), 8.081 (t, 1H, J 5.9 Hz, COCH$_2$NHCO), 9.961 (s, 1H, NHAr).

Ac$_4$(OMe)Neu5Ac-Gab-AC$_3$-Ad-ONp (11) (D$_6$-DMSO, δ, ppm): 1.214, 1.360, 1.478, 1.609 (m, CH$_2$), 2.639 (t, 2H, J 7 Hz, CH$_2$CH$_2$COO), 2.999 (m, 6H, 3CH$_2$NCHO), 3.864 (d, 2H, J$_{NH}$ 5.9 Hz, COCH$_2$NCHO), 4.324 and 4.645 (d, 2×1H, J 11.7 Hz, OCH$_2$Ar), 7.212 and 7.568 (d, 2×2H, J 8.4 Hz, p-C$_6$H$_4$NH), 7.435 and 8.295 (d, 2×2H, J 9.2 Hz, p-C$_6$H$_4$NO$_2$), 7.700 (m, 2H, 2CH$_2$CH$_2$NHCO), 7.750 (t, 1H, J 5.8 Hz, CH$_2$CH$_2$NHCO), 8.122 (t, 1H, J 5.9 Hz, COCH$_2$NHCO), 10.047 (s, 1H, NHAr), Neu5Acα fragment: see (10).

EXAMPLE 3

Preparation of Neu5Acα2-3Galβ1-4Glcβ-NHCOCH$_2$NHCO(CH$_2$)$_4$COO(4-C$_6$H$_4$NO$_2$) (14)

119 mg (0.172 mmol) of compound (12) in 0.5 ml of DMSO were added, while stirring, to a solution of 334 mg (0.86 mmol) of compound (3) in 2 ml of DMF. The mixture was stirred at 20° C. for 24 hours. After the addition of 200 µl of AcOH, the reaction mixture was diluted with 15 ml of water. The solution was filtered and the filtrate was concentrated to a volume of ~2 ml. The residue was poured onto a Sephadex LH-20 column (1.5×50 cm) and eluted with MeCN/H$_2$O (1:1, 0.2% AcOH). After isolation, 140 mg of (14) were obtained, corresponding to a yield of 87%. TLC: R$_f$ 0.41 (eluant H).

$^1$H-NMR spectrum (D$_2$O, δ, ppm): 1.737 (m, 1H, CH$_2$C H$_2$CH$_2$CO), 1.779 (dd, 1H, H-3$_{ax}$ Neu5Ac, J$_4$ 12.5 Hz), 2.003 (s, 3H, NAc), 2.383 (t, 1H, J 7 Hz, CH$_2$CO), 2.733 (dd, 1H, H-3$_{eq}$ Neu5Ac, J$_{3ax}$ 12.5 Hz, J$_4$ 4.5 Hz), 3.432 (m, 1H, H-2 Glc, J$_3$ 9 Hz), 3.556 (dd, 1H, H-2 Gal), 3.933 (dd, 1H, H-4 Gal), 4.090 (dd, 1H, H-3 Gal, J$_2$ 10 Hz, J$_4$ 3 Hz), 4.499 (d, 1H, H-1 Gal, J$_2$ 8 Hz), 4.985 (d, 1H, H-1 Glc, J$_2$ 9 Hz).

The compound Neu5Ac-Gab-Ad-ONp (15) was prepared analogously starting from (3) and Neu5Acα-OCH$_2$ (p-C$_6$H$_4$)—NHCOCH$_2$NH$_2$ (U.S. Pat. No. 5,571,836, 1996).

$^1$H-NMR spectrum (CD$_3$OD, δ, ppm): 1.968 (dd, 1H, H-3$_{ax}$ Neu5Ac), 1.980 (m, 4H, CH$_2$CH$_2$CH$_2$CO), 2.205 (s, 3H, NCOCH$_3$), 2.565 and 2.874 (t, 2×2H, J 6.8 Hz, 2 CH$_2$CO), 2.976 (dd, 1H, J$_4$ 4.5 Hz, J$_{3ax}$ 13 Hz, H-3$_{eq}$ Neu5Ac), 3.743 (dd, 1H, J$_6$ 1.5 Hz, J$_8$ 9 Hz, H-7 Neu5Ac), 3.821 (dd, 1H, J$_5$ 10 Hz, H-6 Neu5Ac), 3.840 (dd, 1H, J$_{9b}$ 12 Hz, J$_8$ 6 Hz, H-9a Neu5Ac), 3.924 (ddd, 1H, H-4 Neu5Ac), 3.978 (ddd, 1H, H-5 Neu5Ac), 4.047 (dd, 1H, J$_8$ 2 Hz, H-9b Neu5Ac), 4.083 (ddd, 1H, H-8 Neu5Ac), 4.196 (s, 2H, COCH$_2$NH), 4.653 and 4.973 (d, 2×1H, J 11 Hz, OC H$_2$Ar), 7.474 and 7.707 (d, 2×2H, J 8.3 Hz, p-C$_6$H$_4$NH), 7.561 and 8.467 (d, 2×2H, J 8.8 Hz, p-C$_6$H$_4$NO$_2$).

The compound of Galα1-3Galβ-O(CH$_2$)$_3$NHCO(CH$_2$)$_4$ COO(p-C$_6$H$_4$NO$_2$) (16) was prepared analogously starting from (3) and Galα1-3Galβ-O(CH$_2$)$_3$NH$_2$ (13).

$^1$H-NMR spectrum (D$_2$O, δ, ppm): 1.78 (m, 4H, CH$_2$CH$_2$), 1.89 (m, 2H, CH$_2$), 2.36 (t, 2H, CH$_2$COO), 2.77 (m, 2H, NHCOCH$_2$), 3.36 (m, 2H, CH$_2$N), 3.69 (t, 1H, J$_3$ 9 Hz, 2-Galβ), 3.76 (m, 1H, OCH'), 3.78 (m, 6,6'-Galα), 3.91 (dd, 1H, J$_3$ 10 Hz, 2-Galα), 4.00 (dd, 1H, 3-Galα), 4.01 (m, 1H, OCH), 4.06 (br. d, 1H, 4-Galα), 4.20 (br. d, 1H, 4-Galβ), 4.23 (br. t, 1H, 5-Galα), 4.48 (dd, 1H, J$_2$ 8 Hz, 1-Galβ), 5.19 (d, 1H, J$_2$ 4 Hz, 1-Galα), 8.38, 7.43 (d, 2×2H, J 9.5 Hz, Ar).

EXAMPLE 4

Tetra-(N-tert-butyloxycarbonyl-pentaglycilamidom-ethyl)methane [BocGly$_5$-NHCH$_2$-]$_4$C (21)

1 mmol of compound (19) (see Table 5) was taken up in 4 ml of CF$_3$COOH and stirred at room temperature for two hours. 4 ml of toluene were added and the reaction mixture was concentrated by evaporation in vacuo and dried. The residue was dissolved in 5 ml of water; 4 ml of a 2M HCl solution were added and concentration was carried out. The resulting tetrahydrochloride (19a) was dried in vacuo and suspended in 0.5 ml of DMF; 6 mmol of BocGlyGlyNOS and 0.5 ml of NEt$_3$ were added and the mixture was stirred at room temperature for 24 hours. The reaction mixture was concentrated in vacuo and the product was purified by column chromatography. After drying in vacuo, compound (21) was obtained in the form of a white powder in a yield of 69% (see Table 5).

Compounds (17)-(20), (22)-(25) were prepared in an analogous manner (see Table 5).

$^1$H-NMR spectra (for the allocation of the $^1$H-NMR signals, the glycines within the chains were numbered, the numbering beginning in each case at the N-terminal end of the chains).

[BocGly-NHCH$_2$-]$_4$C (17). $^1$H-NMR spectrum in D$_6$-DMSO (δ, ppm): 1.366 (s, 9H, OCMe$_3$), 2.759 (br. d, 2H, CCH$_2$), 3.494 (d, 2H, J$_{NH}$ 6 Hz, CH$_2$$^{Gly}$), 7.368 (t, 1H, NH$^{Gly}$), 7.969 (br. t, 1H, CCH$_2$NH), mass spectrum: 783 (M+Na).

[HCl.H-Gly$_2$-NHCH$_2$-]$_4$C (18a). $^1$H-NMR spectrum in D$_2$O (δ, ppm): 2.952 (s, 2H, CCH$_2$), 3.966 (s, 2H, CH$_2$$^{Gly}$), 4.013 (s, 2H, CH$_2$$^{Gly}$).

[BocGly$_3$-NHCH$_2$-]$_4$C (19). $^1$H-NMR spectrum in D$_6$-DMSO (δ, ppm): 1.375 (s, 9H, OCMe$_3$), 2.690 (br. d, 2H, J$_{NH}$ 6.5 Hz, CCH$_2$), 3.586 (d, 2H, J$_{NH}$ 6 Hz, CH$_2$$^{Gly3}$), 3.725 (d, 2H, J$_{NH}$ 5.5 Hz, CH$_2$$^{Gly1}$), 3.847 (d, 2H, J$_{NH}$ 5.5 Hz, CH$_2$$^{Gly2}$), 6.976 (t, 1H, NH$^{Gly3}$), 7.811 (t, 1H, NH$^{Gly2}$), 7.975 (t, 1H, CCH$_2$NH), 8.534 (t, 1H, NH$^{Gly1}$), mass spectrum: 1239 (M+Na).

[BocGly$_4$-NHCH$_2$-]$_4$C (20). $^1$H-NMR spectrum in D$_6$-DMSO (δ, ppm): 1.374 (s, 9H, OCMe$_3$), 2.694 (br. d, 2H, CCH$_2$), 3.575 (d, 2H, CH$_2$$^{Gly4}$), 3.707 (d, 2H, CH$_2$$^{Gly1}$), 3.750 (d, 2H, CH$_2$$^{Gly3}$), 3.835 (d, 2H, CH$_2$$^{Gly2}$), 6.980 (t, 1H, NH$^{Gly4}$), 7.827 (t, 1H, CCH$_2$NH), 8.048 (t, 1H, NH$^{Gly3}$), 8.096 (t, 1H, NH$^{Gly2}$), 8.590 (t, 1H, NH$^{Gly1}$), mass spectrum: 1467 (M+Na).

[BocGly$_5$-NHCH$_2$-]$_4$C (21). $^1$H-NMR spectrum in D$_6$-DMSO (δ, ppm): 1.380 (s, 9H, OCMe$_3$), 2.688 (br. d, 2H, CCH$_2$), 3.579 (d, 2H, J$_{NH}$ 6 Hz, CH$_2$$^{Gly5}$), 3.718 (d, 2H, J$_{NH}$ 5 Hz, CH$_2$$^{Gly1}$), 3.750 (d, 4H, J$_{NH}$~5 Hz, CH$_2$$^{Gly3,4}$), 3.840 (d, 2H, J$_{NH}$ 5.5 Hz, CH$_2$$^{Gly2}$), 6.974 (t, 1H, NH$^{Gly5}$), 7.770 (t, 1H, CCH$_2$NH), 8.006 (t, 1H, NH$^{Gly4}$), 8.075 and 8.102 (t, 1H, NH$^{Gly2,3}$), 8.550 (t, 1H, NH$^{Gly1}$), mass spectrum: 1695 (M+Na), 1711 (M+K).

[BocGly$_7$-NHCH$_2$-]$_4$C (22). $^1$H-NMR spectrum in D$_6$-DMSO (δ, ppm): 1.378 (s, 9H, OCMe$_3$), 2.688 (br., 2H, CCH$_2$), 3.581 (d, 2H, CH$_2$$^{Gly7}$), 3.723 (br. d, 2H, CH$_2$$^{Gly1}$), 3.751 (m, 8H, CH$_2$$^{Gly3-6}$), 3.840 (br. d, 2H, CH$_2$$^{Gly2}$), 6.970 (br. t, 1H, NH$^{Gly7}$), 7.814 (br. t, 1H, CCH$_2$NH), 8.018 (br. t, 1H, NH$^{Gly6}$), 8.081, 8.085, 8.092 and 8.118 (m, 4H, NH$^{Gly2-5}$), 8.545 (br. t, 1H, NH$^{Gly1}$).

[HCl.H-AC-Gly$_5$-NHCH$_2$-]$_4$C (23a). $^1$H-NMR spectrum in D$_2$O (δ, ppm): 1.446 (m, 2H, CH$_2$), 1.689 (m, 2H, COCH$_2$CH$_2$), 1.724 (m, 2H, CH$_2$CH$_2$N), 2.398 (t, 2H, J 7.4 Hz, COCH$_2$), 2.967 (br. s, CCH$_2$), 3.044 (t, 2H, J 7.4 Hz, CH$_2$N), 3.944, 4.012, 4.049 (x2) and 4.096 (s, 10H, 5 COCH$_2$N).

[HCl.H-AC$_2$-Gly$_5$-NHCH$_2$-]$_4$C (24a). $^1$H-NMR spectrum in D$_2$O (δ, ppm): 1.336 and 1.382 (m, 4H, 2 CH$_2$), 1.548 (m, 2H, CH$_2$CH$_2$N), 1.656 (m, 4H, 2 COCH$_2$CH$_2$), 1.712 (m, 2H, CH$_2$CH$_2$N$^+$), 2.283 (t, 2H, J 7.4 Hz, COCH$_2$), 2.370 (t, 2H, J 7.4 Hz, COCH$_2$NHCOCH$_2$), 2.955 (br. s, CCH$_2$), 3.031 (t, 2H, J 7.4 Hz, CH$_2$N$^+$), 3.206 (t, 2H, J 6.6 Hz, CH$_2$N), 3.988, 4.00, 4.044 (x2) and 4.091 (s, 10H, 5 COCH$_2$N).

[HCl.H-AC$_3$-Gly$_5$-NHCH$_2$-]$_4$C (25a). $^1$H-NMR spectrum in D$_2$O (δ, ppm): 1.34-1.42 (m, 6H, 3 CH$_2$), 1.551 (m, 4H, 2 CH$_2$CH$_2$N), 1.653 (x2) and 1.689 (m, 6H, COCH$_2$CH$_2$), 1.717 (m, 2H, CH$_2$CH$_2$N$^+$), 2.270 and 2.288 (t, 4H, J 7.5 Hz, 2 COCH$_2$), 2.376 (t, 2H, J 7.5 Hz, COCH$_2$NHCOCH$_2$), 2.952 (br. s, CCH$_2$), 3.033 (t, 2H, J 7.5 Hz, CH$_2$N$^+$), 3.208 (t, 4H, J 7 Hz, 2CH$_2$N), 3.990, 4.004, 4.049 (x2) and 4.097 (s, 10H, 5 COCH$_2$N).

TABLE 5

Preparation of tetravalent matrices (17)-(25) (Example 4)

| End product | Starting compound | Carboxylate | Conditions | TLC Boc derivative RF | Eluant | Tetrahydrochloride Rf | Eluant | Isolation of the products | Yield % |
|---|---|---|---|---|---|---|---|---|---|
| [BocGly-NHCH$_2$—]$_4$C (17) | (1) | 6 mM BocGlyNOS | 24 hours stirring in DMF at room temperature | 0.5 | D | 0.72 | F | The reaction mixture was concentrated by evaporation in vacuo and (17) obtained by crytallisation from trifluoromethanol after addition of CHCl$_3$/ethyl acetate/MeOH (9/3/1). | 78 |
| [BocGly$_2$-NHCH$_2$—]$_4$C (18) | (1) | 6 mM BocGlyGlyNOS | | — | — | 0.72 | | The product (18) is only very slightly soluble, it was isolated by filtration and, after removal of the Boc protecting groups, identified as tetrahydrochloride (18a) | 95 |
| [BocGly$_3$-NHCH$_2$—]$_4$C (19) | (17) | | | 0.79 | acetone/MeOH/H$_2$O 15:1:1 | 0.61 | | The reaction mixture was concentrated by evaporation in vacuo Column chromatography: acetone/MeOH/H$_2$O 30:1:1→15:1:1. | 77 |
| [BocGly$_4$-NHCH$_2$—]$_4$C (20) | (18) | | | 0.48 | E | 0.55 | | The reaction mixture was concentrated by evaporation in vacuo. Column chromatography: acetone/MeOH/H$_2$O 30:1:1→10:1:1 | 63 |
| [BocGly$_5$-NHCH$_2$—]$_4$C (21) | (19) | | | 0.36 | | 0.33 | | | 69 |
| [BocGly$_7$-NHCH$_2$—]$_4$C (22) | (21) | | | — | — | 0.67 | 2N HCl | The product (22) is only very slightly soluable, it was isolated by filtration and, after removal of the Boc protecting groups, identified as tetrahydrochloride (22a) | 93 |
| [Boc-AC-Gly$_5$-NHCH$_2$—]$_4$C (23) | (21) | 12 mM BocNH(CH$_2$)$_5$-COONp | DMSO, 70° C. 72 hours | 0.38 | G | 0.22 | | The products after chromatography over Sephadex LH-20, MeCN/H$_2$O 1:1 and after removal of the Boc protecting groups, identified as tetrahydrochloride (23a), (24a) and (25a) | 71 |
| [Boc-AC$_2$-Gly$_5$-NHCH$_2$—]$_4$C (24) | (23) | | | 0.73 | | 0.1 | | | 57 |
| [Boc-AC$_3$-Gly$_5$-NHCH$_2$—]$_4$C (25) | (24) | | | 0.4 | | — | | | 40 |

EXAMPLE 5

Preparation of Protected Tetrasialosides

Preparation of [Ac$_4$(OMe)Neu5Acα-OCH$_2$(p-C$_6$H$_4$)NHCOCH$_2$NH-CO(CH$_2$)$_4$CO-(NHCH$_2$CO)$_5$NHCH$_2$]$_4$C

[Ac$_4$(OMe)Neu5Ac-Gab-Ad-Gly$_5$-NHCH$_2$-]$_4$C (31).

1 mmol of compound (21) (see Table 6) was taken up in 4 ml of CF$_3$COOH and the mixture was stirred at room temperature for two hours. 4 ml of toluene were added and the reaction mixture was concentrated by evaporation in vacuo and dried. The residue was dissolved in 5 ml of water; 4 ml of a 2M HCl solution were added and the mixture was concentrated. The resulting tetrahydrochloride (21a) was dried in vacuo and suspended in 0.5 ml of DMF; 6 mmol of Ac$_4$(OMe)Neu5Ac-Gab-Ad-ONp (8) and 0.5 ml of NEt$_3$ were added and the mixture was stirred at room temperature for 24 hours. The reaction mixture was concentrated in vacuo and the product was purified by means of column chromatography (see Table 6). After drying in vacuo, the compound (21) was obtained in the form of a colourless amorphous product in a yield of 65%.

Compounds (26)-(30), (32)-(36) were prepared in an analogous manner (see Table 6).

[Ac$_4$(OMe)Neu5Ac-Gab-Ad-NHCH$_2$-]$_4$C (26). $^1$H-NMR spectrum in D$_6$-DMSO (δ, ppm): matrix: 1.534 (m, 4H, 2 COCH$_2$C$\underline{H}_2$), 2.171 (m, 4H, 2 COC$\underline{H}_2$CH$_2$), 2.891 (br., 2H, CCH$_2$), 3.867 (d, 2H, ArNHCOC$\underline{H}_2$), 7.674 (br. t, 1H, CCH$_2$N$\underline{H}$), 8.107 (t, 1H, J 6 Hz, N$\underline{H}$COCH$_2$CH$_2$), 9.964 (s, 1H, ArNH); Neu5Acα2-OCH$_2$C$_6$H$_4$ fragment: 1.677, 1.918, 1.975, 2.024 and 2.094 (s, 15H, 5 COCH$_3$), 1.761 (dd, 1H, J$_4$ 12.2 Hz, H-3ax), 2.570 (dd, 1H, J$_{3ax}$ 12.5 Hz, J$_4$ 4.6 Hz, H-3eq), 3.697 (s, 3H, COOCH$_3$), 3.904 (ddd, 1H, J$_4$ 10.3 Hz, H-5), 4.028 (dd, 1H, J$_8$ 6.3 Hz, H-9b), 4.087 (dd, 1H, J$_5$ 10.7 Hz, H-6), 4.233 (dd, 1H, J$_{9b}$ 12.5 Hz, J$_8$ 3 Hz, H-9a), 4.320 and 4.643 (d, 2H, J 11.8 Hz, ArCH$_2$), 4.711 (ddd, 1H, H-4), 5.192 (dd, 1H, J$_8$ 8.4 Hz, J$_6$ 2.4 Hz, H-7), 5.341 (ddd, 1H, H-8), 7.214 and 7.555 (d, 2H, J 8.6 Hz, Ar), 7.708 (d, 1H, J$_5$ 9.6 Hz, NH).

[Ac$_4$(OMe)Neu5Ac-Gab-Ad-Gly-NHCH$_2$-]$_4$C (27). $^1$H-NMR spectrum in D$_6$-DMSO (δ, ppm): matrix: 1.509 (m, 4H, 2 COCH$_2$CH$_2$), 2.147 and 2.231 (m, 4H, 2 COCH$_2$CH$_2$), 2.674 (br., 2H, CCH$_2$), 3.647 (m, 2H, Gly), 3.859 (d, 2H, ArNHCOCH$_2$), 7.852 (br. t, 1H, CCH$_2$NH), 8.100 (t, 1H, J 6 Hz, NHCOCH$_2$CH$_2$), 8.453 (t, 1H, J 6 Hz, NHGly), 9.962 (s, 1H, ArNH), Neu5Acα2-OCH$_2$C$_6$H$_4$ fragment: 1.677, 1.918, 1.975, 2.024 and 2.094 (s, 15H, 5 COCH$_3$), 1.761 (dd, 1H, J$_4$ 12.2 Hz, H-3ax), 2.570 (dd, 1H, J$_{3ax}$ 12.5 Hz, J$_4$ 4.6 Hz, H-3eq), 3.697 (s, 3H, COOCH$_3$), 3.904 (ddd, 1H, J$_4$ 10.3 Hz, H-5), 4.028 (dd, 1H, J$_8$ 6.3 Hz, H-9b), 4.087 (dd, 1H, J$_5$ 10.7 Hz, H-6), 4.233 (dd, 1H, J$_{9b}$ 12.5 Hz, J$_8$ 3 Hz, H-9a), 4.320 and 4.643 (d, 2H, J 11.8 Hz, ArCH$_2$), 4.711 (ddd, 1H, H-4), 5.192 (dd, 1H, J$_8$ 8.4 Hz, J$_6$ 2.4 Hz, H-7), 5.341 (ddd, 1H, H-8), 7.214 and 7.555 (d, 2H, J 8.6 Hz, Ar), 7.708 (d, 1H, J$_5$ 9.6 Hz, NH).

[Ac$_4$(OMe)Neu5Ac-Gab-Ad-Gly$_2$-NHCH$_2$-]$_4$C (28). $^1$H-NMR spectrum in D$_6$-DMSO (δ, ppm): matrix: 1.495 (m, 4H, 2 COCH$_2$CH$_2$), 2.150 (m, 4H, 2 COCH$_2$CH$_2$), 2.694 (br., 2H, CCH$_2$), 3.716 (d, 2H, CH$_2^{Gly2}$), 3.818 (d, 2H, CH$_2^{Gly1}$), 3.865 (d, 2H, ArNHCOCH$_2$), 7.824 (br. t, 1H, CCH$_2$NH), 7.933 (t, 1H, J 6 Hz, NH$^{Gly2}$), 8.096 (t, 1H, J 6 Hz, NHCOCH$_2$CH$_2$), 8.544 (t, 1H, J 6 Hz, NH$^{Gly1}$), 9.975 (s, 1H, ArNH). Neu5Acα2-OCH$_2$C$_6$H$_4$ fragment: 1.677, 1.918, 1.975, 2.024 and 2.094 (s, 15H, 5 COCH$_3$), 1.761 (dd, 1H, J$_4$ 12.2 Hz, H-3ax), 2.570 (dd, 1H, J$_{3ax}$ 12.5 Hz, J$_4$ 4.6 Hz, H-3eq), 3.697 (s, 3H, COOCH$_3$), 3.904 (ddd, 1H, J$_4$ 10.3 Hz, H-5), 4.028 (dd, 1H, J$_8$ 6.3 Hz, H-9b), 4.087 (dd, 1H, J$_5$ 10.7 Hz, H-6), 4.233 (dd, 1H, J$_{9b}$ 12.5 Hz, J$_8$ 3 Hz, H-9a), 4.320 and 4.643 (d, 2H, J 11.8 Hz, ArCH$_2$), 4.711 (ddd, 1H, H-4), 5.192 (dd, 1H, J$_8$ 8.4 Hz, J$_6$ 2.4 Hz, H-7), 5.341 (ddd, 1H, H-8), 7.214 and 7.555 (d, 2H, J 8.6 Hz, Ar), 7.708 (d, 1H, J$_5$ 9.6 Hz, NH).

[Ac$_4$(OMe)Neu5Ac-Gab-Ad-Gly$_3$-NHCH$_2$]$_4$C (29). $^1$H-NMR spectrum in D$_6$-DMSO (δ, ppm): matrix: 1.498 (m, 4H, 2 COCH$_2$CH$_2$), 2.143 and 2.158 (m, 4H, 2 COCH$_2$CH$_2$), 2.693 (br., 2H, CCH$_2$), 3.728 (m, 4H, 2 CH$_2^{Gly2,3}$), 3.841 (d, 2H, CH$_2^{Gly1}$), 3.862 (d, 2H, ArNHCOCH$_2$), 7.820 (br. t, 1H, CCH$_2$NH), 8.049 and 8.059 (t, 2H, J 5.7 Hz, NH$^{Gly2,3}$), 8.098 (t, 1H, J 5.8 Hz, NHCOCH$_2$CH$_2$), 8.547 (t, 1H, J 5.5 Hz, NH$^{Gly1}$), 9.972 (s, 1H, ArNH). Neu5Acα2-OCH$_2$C$_6$H$_4$ fragment: 1.677, 1.918, 1.975, 2.024 and 2.094 (s, 15H, 5 COCH$_3$), 1.761 (dd, 1H, J$_4$ 12.2 Hz, H-3ax), 2.570 (dd, 1H, J$_{3ax}$ 12.5 Hz, J$_4$ 4.6 Hz, H-3eq), 3.697 (s, 3H, COOCH$_3$), 3.904 (ddd, 1H, J$_4$ 10.3 Hz, H-5), 4.028 (dd, 1H, J$_8$ 6.3 Hz, H-9b), 4.087 (dd, 1H, J$_5$ 10.7 Hz, H-6), 4.233 (dd, 1H, J$_{9b}$ 12.5 Hz, J$_8$ 3 Hz, H-9a), 4.320 and 4.643 (d, 2H, J 11.8 Hz, ArCH$_2$), 4.711 (ddd, 1H, H-4), 5.192 (dd, 1H, J$_8$ 8.4 Hz, J$_6$ 2.4 Hz, H-7), 5.341 (ddd, 1H, H-8), 7.214 and 7.555 (d, 2H, J 8.6 Hz, Ar), 7.708 (d, 1H, J$_5$ 9.6 Hz, NH).

[Ac$_4$(OMe)Neu5Ac-Gab-Ad-Gly$_4$-NHCH$_2$]$_4$C (30). $^1$H-NMR spectrum in D$_6$-DMSO (δ, ppm): matrix: 1.500 (m, 4H, 2 COCH$_2$CH$_2$), 2.151 (m, 4H, 2 COCH$_2$CH$_2$), 2.688 (br., 2H, CCH$_2$), 3.720 (x2) and 3.753 (d, 6H, 3 CH$_2^{Gly2-4}$), 3.841 (d, 2H, CH$_2^{Gly1}$), 3.864 (d, 2H, ArNHCOCH$_2$), 7.818 (br. t, 1H, CCH$_2$NH), 8.045 and 8.084 (x2), (t, 3H, J 6 Hz, NH$^{Gly2-4}$), 8.102 (t, 1H, J 6 Hz, NHCOCH$_2$CH$_2$), 8.555 (t, 1H, J 5.5 Hz, NH$^{Gly1}$), 9.980 (s, 1H, ArNH). Neu5Acα2-OCH$_2$C$_6$H$_4$ fragment: 1.677, 1.918, 1.975, 2.024 and 2.094 (s, 15H, 5 COCH$_3$), 1.761 (dd, 1H, J$_4$ 12.2 Hz, H-3ax), 2.570 (dd, 1H, J$_{3ax}$ 12.5 Hz, J$_4$ 4.6 Hz, H-3eq), 3.697 (s, 3H, COOCH$_3$), 3.904 (ddd, 1H, J$_4$ 10.3 Hz, H-5), 4.028 (dd, 1H, J$_8$ 6.3 Hz, H-9b), 4.087 (dd, 1H, J$_5$ 10.7 Hz, H-6), 4.233 (dd, 1H, J$_{9b}$ 12.5 Hz, J$_8$ 3 Hz, H-9a), 4.320 and 4.643 (d, 2H, J 11.8 Hz, ArCH$_2$), 4.711 (ddd, 1H, H-4), 5.192 (dd, 1H, J$_8$ 8.4 Hz, J$_6$ 2.4 Hz, H-7), 5.341 (ddd, 1H, H-8), 7.214 and 7.555 (d, 2H, J 8.6 Hz, Ar), 7.708 (d, 1H, J$_5$ 9.6 Hz, NH).

[Ac$_4$(OMe)Neu5Ac-Gab-Ad-Gly$_5$-NHCH$_2$]$_4$C (30). $^1$H-NMR spectrum in D$_6$-DMSO (δ, ppm): matrix: 1.502 (m, 4H, 2 COCH$_2$CH$_2$), 2.147 and 2.159 (m, 4H, 2 COCH$_2$CH$_2$), 2.688 (br., 2H, CCH$_2$), 3.738 (x2) and 3.765 (x2) (m, 8H, 4 CH$_2^{Gly2-5}$), 3.857 (d, 2H, CH$_2^{Gly1}$), 3.877 (d, 2H, ArNHCOCH$_2$), 7.818 (br. t, 1H, CCH$_2$NH), 8.074 (m, 5H, NHCOCH$_2$CH$_2$, NH$^{Gly2-5}$), 8.551 (t, 1H, J 6 Hz, NH$^{Gly1}$), 9.968 (s, 1H, ArNH). Neu5Acα2-OCH$_2$C$_6$H$_4$ fragment: 1.677, 1.918, 1.975, 2.024 and 2.094 (s, 15H, 5 COCH$_3$), 1.761 (dd, 1H, J$_4$ 12.2 Hz, H-3ax), 2.570 (dd, 1H, J$_{3ax}$ 12.5 Hz, J$_4$ 4.6 Hz, H-3eq), 3.697 (s, 3H, COOCH$_3$), 3.904 (ddd, 1H, J$_4$ 10.3 Hz, H-5), 4.028 (dd, 1H, J$_8$ 6.3 Hz, H-9b), 4.087 (dd, 1H, J$_5$ 10.7 Hz, H-6), 4.233 (dd, 1H, J$_{9b}$ 12.5 Hz, J$_8$ 3 Hz, H-9a), 4.320 and 4.643 (d, 2H, J 11.8 Hz, ArCH$_2$), 4.711 (ddd, 1H, H-4), 5.192 (dd, 1H, J$_8$ 8.4 Hz, J$_6$ 2.4 Hz, H-7), 5.341 (ddd, 1H, H-8), 7.214 and 7.555 (d, 2H, J 8.6 Hz, Ar), 7.708 (d, 1H, J$_5$ 9.6 Hz, NH).

[Ac$_4$(OMe)Neu5Ac-Gab-Ad-AC$_2$-Gly$_5$-NHCH$_2$]$_4$C (32). $^1$H-NMR spectrum in D$_6$-DMSO (δ, ppm), matrix: 1.224, 1.366 and 1.469 (m, 12H, 6 CH$_2$), 1.502 (m, 4H, 2 COCH$_2$CH$_2$), 2.032 and 2.121 (m, 2 COCH$_2$), 2.147 and 2.159 (m, 4H, 2 COCH$_2$CH$_2$), 2.688 (br., 2H, CCH$_2$), 3.00 (m, 4H, 2 CH$_2$NHCO), 3.738 (x2) and 3.765 (x2) (m, 8H, 4 CH$_2^{Gly2-5}$), 3.857 (d, 2H, CH$_2^{Gly1}$), 3.877 (d, 2H, ArNHCOCH$_2$), 7.679 and 7.700 (br. t, 2H, 2 NHCO), 7.818 (br. t, 1H, CCH$_2$NH), 8.074 (m, 5H, NHCOCH$_2$CH$_2$, NH$^{Gly2-5}$), 8.551 (t, 1H, J 6 Hz, NH$^{Gly1}$), 9.968 (s, 1H, ArNH). Neu5Acα2-OCH$_2$C$_6$H$_4$ fragment: 1.677, 1.918, 1.975, 2.024 and 2.094 (s, 15H, 5 COCH$_3$), 1.761 (dd, 1H, J$_4$ 12.2 Hz, H-3ax), 2.570 (dd, 1H, J$_{3ax}$ 12.5 Hz, J$_4$ 4.6 Hz, H-3eq), 3.697 (s, 3H, COOCH$_3$), 3.904 (ddd, 1H, J$_4$ 10.3 Hz, H-5), 4.028 (dd, 1H, J$_8$ 6.3 Hz, H-9b), 4.087 (dd, 1H, J$_5$ 10.7 Hz, H-6), 4.233 (dd, 1H, J$_{9b}$ 12.5 Hz, J$_8$ 3 Hz, H-9a), 4.320 and 4.643 (d, 2H, J 11.8 Hz, ArCH$_2$), 4.711 (ddd, 1H, H-4), 5.192 (dd, 1H, J$_8$ 8.4 Hz, J$_6$ 2.4 Hz, H-7), 5.341 (ddd, 1H, H-8), 7.214 and 7.555 (d, 2H, J 8.6 Hz, Ar), 7.708 (d, 1H, J$_5$ 9.6 Hz, NH).

[Ac$_4$(OMe)Neu5Ac-Gab-Ad-AC$_3$-Gly$_5$-NHCH$_2$]$_4$C (33). $^1$H-NMR spectrum in D$_6$-DMSO (δ, ppm) is very similar to the spectrum of compound (32) (the signals are in some cases broader and the integrals of the amidocaproic acid groups are corresponding greater).

[Ac$_4$(OMe)Neu5Ac-Gab-AC-Ad-Gly$_5$-NHCH$_2$]$_4$C (34). $^1$H-NMR spectrum in D$_6$-DMSO (δ, ppm): matrix: 1.25, 1.382, 1.465 and 1.506 (m, 10H, 5 CH$_2$), 2.033 and 2.140 (m, 6H, 3 COCH$_2$), 2.697 (br., 2H, CCH$_2$), 3.009 (m~q, 2H, J 6.4 Hz, CH$_2$NHCO), 3.719 (x2) and 3.748 (x2) (m, 8H, 4 CH$_2^{Gly2-5}$), 3.843 (d, 2H, CH$_2^{Gly1}$), 3.862 (d, 2H, ArNHCOCH$_2$), 4.327 and 4.648 (d, 2H, J 11.8 Hz, ArCH$_2$), 7.216 and 7.555 (d, 2H, J 8 Hz, Ar), 7.698 (t, 1H, NHCO), 7.818 (br. t, 1H, CCH$_2$NH), 8.039, 8.072, 8.084 (x2), 8.110 (m, 5H, NHCOCH$_2$CH$_2$, NH$^{Gly2-5}$), 8.547 (t, 1H, NH$^{Gly1}$), 9.970 (s, 1H, ArNH). Neu5Acα2-OCH$_2$C$_6$H$_4$ fragment: 1.677, 1.918, 1.975, 2.024 and 2.094 (s, 15H, 5 COCH$_3$), 1.761 (dd, 1H, J$_4$ 12.2 Hz, H-3ax), 2.570 (dd, 1H, J$_{3ax}$ 12.5 Hz, J$_4$ 4.6 Hz, H-3eq), 3.697 (s, 3H, COOCH$_3$), 3.904 (ddd, 1H, J$_4$ 10.3 Hz, H-5), 4.028 (dd, 1H, J$_8$ 6.3 Hz, H-9b), 4.087 (dd, 1H, J$_5$ 10.7 Hz, H-6), 4.233 (dd, 1H, J$_{9b}$ 12.5 Hz, J$_8$ 3 Hz, H-9a), 4.320 and 4.643 (d, 2H, J 11.8 Hz, ArCH$_2$), 4.711 (ddd, 1H, H-4), 5.192 (dd, 1H, J$_8$ 8.4 Hz, J$_6$ 2.4 Hz, H-7), 5.341 (ddd, 1H, H-8), 7.214 and 7.555 (d, 2H, J 8.6 Hz, Ar), 7.708 (d, 1H, $J_5$ 9.6 Hz, NH).

[Ac$_4$(OMe)Neu5Ac-Gab-AC$_2$-Ad-Gly$_5$-NHCH$_2$]$_4$C (35). $^1$H-NMR spectrum in D$_6$-DMSO (δ, ppm): matrix: 1.239, 1.375, 1.465 and 1.509 (m, CH$_2$), 2.026 and 2.142 (m, COCH$_2$), 2.711 (br., 2H, CCH$_2$), 3.003 (m, 4H, 2 CH$_2$NHCO), 3.718 (x2) and 3.746 (x2) (m, 8H, 4 CH$_2^{Gly2-5}$), 3.839 (d, 2H, CH$_2^{Gly1}$), 3.861 (d, 2H, ArNHCOCH$_2$), 4.329 and 4.649 (d, 2H, J 11.8 Hz, ArCH$_2$), 7.218 and 7.561 (d, 2H, J 8 Hz, Ar), 7.681 and 7.695 (m, 2H, 2 NHCO), 7.834 (br. t, 1H, CCH$_2$NH), 8.077, 8.133 (x3), 8.177 (m, 5H, NHCOCH$_2$CH$_2$, NH$^{Gly2-5}$), 8.587 (t, 1H, NH$^{Gly1}$), 10.01 (s, 1H, ArNH). Neu5Acα2-OCH$_2$C$_6$H$_4$ fragment: 1.677, 1.918, 1.975, 2.024 and 2.094 (s, 15H, 5 COCH$_3$), 1.761 (dd, 1H, $J_4$ 12.2 Hz, H-3ax), 2.570 (dd, 1H, $J_{3ax}$ 12.5 Hz, $J_4$ 4.6 Hz, H-3eq), 3.697 (s, 3H, COOCH$_3$), 3.904 (ddd, 1H, $J_4$ 10.3 Hz, H-5), 4.028 (dd, 1H, $J_8$ 6.3 Hz, H-9b), 4.087 (dd, 1H, $J_5$ 10.7 Hz, H-6), 4.233 (dd, 1H, $J_{9b}$ 12.5 Hz, $J_8$ 3 Hz, H-9a), 4.320 and 4.643 (d, 2H, J 11.8 Hz, ArCH$_2$), 4.711 (ddd, 1H, H-4), 5.192 (dd, 1H, $J_8$ 8.4 Hz, $J_6$ 2.4 Hz, H-7), 5.341 (ddd, 1H, H-8), 7.214 and 7.555 (d, 2H, J 8.6 Hz, Ar), 7.708 (d, 1H, $J_5$ 9.6 Hz, NH).

[Ac$_4$(OMe)Neu5Ac-Gab-AC$_3$-Ad-Gly$_5$-NHCH$_2$]$_4$C (36). The $^1$H-NMR spectrum in D$_6$-DMSO corresponds very substantially to the spectrum of compound (35), the signals are in some cases broader. Matrix (δ, ppm): 1.239, 1.375, 1.465 and 1.509 (m, CH$_2$), 2.026 and 2.142 (m, COCH$_2$), 2.629 (br., 2H, CCH$_2$), 3.00 (m, 6H, 3 CH$_2$NHCO), 3.813 (br., 2H, CH$_2^{Gly1}$), 3.861 (d, 2H, ArNHCOCH$_2$), 4.329 and 4.649 (d, 2H, J 11.8 Hz, ArCH$_2$), 7.218 and 7.561 (d, 2H, J 8 Hz, Ar), 7.693 (m, 3H, 3 NHCO), 7.904 (br., 1H, CCH$_2$NH), 8.083 (x2), 8.158 and 8.215 (x2) (m, 5H, NHCOCH$_2$CH$_2$, NH$^{Gly2-5}$), 8.538 (t, 1H, NH$^{Gly1}$). Neu5Acα2-OCH$_2$C$_6$H$_4$ fragment: 1.677, 1.918, 1.975, 2.024 and 2.094 (s, 15H, 5 COCH$_3$), 1.761 (dd, 1H, $J_4$ 12.2 Hz, H-3ax), 2.570 (dd, 1H, $J_{3ax}$ 12.5 Hz, $J_4$ 4.6 Hz, H-3eq), 3.697 (s, 3H, COOCH$_3$), 3.904 (ddd, 1H, $J_4$ 10.3 Hz, H-5), 4.028 (dd, 1H, $J_8$ 6.3 Hz, H-9b), 4.087 (dd, 1H, $J_5$ 10.7 Hz, H-6), 4.233 (dd, 1H, $J_{9b}$ 12.5 Hz, $J_8$ 3 Hz, H-9a), 4.320 and 4.643 (d, 2H, J 11.8 Hz, ArCH$_2$), 4.711 (ddd, 1H, H-4), 5.192 (dd, 1H, $J_8$ 8.4 Hz, $J_6$ 2.4 Hz, H-7), 5.341 (ddd, 1H, H-8), 7.214 and 7.555 (d, 2H, J 8.6 Hz, Ar), 7.708 (d, 1H, $J_5$ 9.6 Hz, NH).

TABLE 6

Preparation of protected tetrasialosides (26)-(36) (Example 5)

| End products Methyl ester peracetate | Matrix | Glycoside | Conditions | TLC Rf | Eluant | Isolation of the products | Yield % |
|---|---|---|---|---|---|---|---|
| [Ac$_4$(OMe)Neu5Ac-Gab-Ad-NHCH$_2$—]$_4$C (26) | (1) | 6 mM (8) | DMF, 24 hours stirring at room temperature | 0.21 | C | Reaction mixture was concentrated by evaporation in vacuo; LC: CHCl$_3$/MeOH 10:1 | 57 |
| [Ac$_4$(OMe)Neu5Ac-Gab-Ad-Gly-NHCH$_2$—]$_4$C (27) | (17) | | | 0.51 | E | Reaction mixture was concentrated by evaporation in vacuo; LC: i-PrOH/EtOAc/H$_2$O 2:5:1 | 66 |
| [Ac$_4$(OMe)Neu5Ac-Gab-Ad-Gly$_2$-NHCH$_2$—]$_4$C (28) | (18) | | | 0.25 | E | Reaction mixture was concentrated by evaporation in vacuo; LC: acetone/MeOH/H$_2$O 20:1:1→5:1:1 | 63 |
| [Ac$_4$(OMe)Neu5Ac-Gab-Ad-Gly$_3$-NHCH$_2$—]$_4$C (29) | (19) | | | 0.23 | E | Reaction mixture was concentrated by evaporation in vacuo; LC: acetone/MeOH/ H$_2$O 30:1:1→10:1:1 | 33 |
| [Ac$_4$(OMe)Neu5Ac-Gab-Ad-Gly$_4$-NHCH$_2$—]$_4$C (30) | (20) | | | 0.40 | G | Reaction mixture was concentrated by evaporation in vacuo; LC: acetone/MeOH/H$_2$O 15:1:1→5:1:1 | 68 |
| [Ac$_4$(OMe)Neu5Ac-Gab-Ad-Gly$_5$-NHCH$_2$—]$_4$C (31) | (21) | | | 0.18 | G | Reaction mixture was concentrated by evaporation in vacuo; LC: acetone/MeOH/H$_2$O 20:1:1→5:1:1 | 65 |
| [Ac$_4$(OMe)Neu5Ac-Gab-Ad-AC$_2$-Gly$_5$-NHCH$_2$—]$_4$C (32) | (24) | 12 mM (8) | DMSO, 70° C. 72 hours | 0.15 | G | Sephadex LH-20, MeCN/H$_2$O 1:1 | 60 |
| [Ac$_4$(OMe)Neu5Ac-Gab-Ad-AC$_3$-Gly$_5$-NHCH$_2$—]$_4$C (33) | (25) | | | 0.45 | H | | 57 |

TABLE 6-continued

Preparation of protected tetrasialosides (26)-(36) (Example 5)

| End products Methyl ester peracetate | Matrix | Glycoside | Conditions | TLC Rf | Eluant | Isolation of the products | Yield % |
|---|---|---|---|---|---|---|---|
| [Ac$_4$(OMe)Neu5Ac-Gab-AC-Ad-Gly$_5$-NHCH$_2$—]$_4$C (34) | (21) | 12 mM (9) | | 0.16 | G | Reaction mixture was lyophilised; LC: eluant G, then i-PrOH/MeOH/EtOAc/H$_2$O 4:3:3:3 | 76 |
| [Ac$_4$(OMe)Neu5Ac-Gab-AC$_2$-Ad-Gly$_5$-NHCH$_2$—]$_4$C (35) | (21) | 12 mM (10) | | 0.11 | G | Reaction mixture was lyophilised, LC: eluant G, then H | 46 |
| [Ac$_4$(OMe)Neu5Ac-Gab-AC$_3$-Ad-Gly$_5$-NHCH$_2$—]$_4$C (36) | (21) | 12 mM (11) | | 0.84 | H | | 11 |

EXAMPLE 6

Preparation of Free Tetrasialosides

Preparation of [Neu5Acα-OCH$_2$(p-C$_6$H$_4$)NHCOCH$_2$NH—CO(CH$_2$)$_4$CO—(NH(CH$_2$)$_5$CO)$_3$—(NHCH$_2$CO)$_5$—NHCH$_2$—]$_4$C (ammonium salt)

Neu5Ac-Gab-Ad-AC$_3$-Gly$_5$-NHCH$_2$]$_4$C (44).

80 μl of 2N NaOH solution were added to a solution of 10 μmol of the protected tetrasialoside (33) in 3 ml of absolute MeOH, and after 3 hours 1.5 ml of water and 80 μl of 2N NaOH solution were again added. The mixture was stirred at room temperature overnight; 80 μl of AcOH were added and the mixture was evaporated to dryness. The product was obtained by means of gel chromatography over Sephadex G-10 using a 0.05M aqueous NH$_4$OH solution. (see Table 7).

Compounds (37)-(43), (45)-(47) were obtained in an analogous manner (see Table 7).

Hz, ArCH$_2$), 7.388 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

[Neu5Ac-Gab-Ad-Gly-NHCH$_2$-]$_4$C (38). $^1$H-NMR spectrum in D$_2$O (δ, ppm): matrix: 1.622 (m, 4H, COCH$_2$CH$_2$), 2.340 and 2.382 (m, 4H, 2 COCH$_2$CH$_2$), 2.810 (s, 2H, CCH$_2$), 3.847 (s, 2H, CH$_2$$^{Gly}$), 4.016 (s, 2H, ArNHCOCH$_2$), 4.492 and 4.707 (d, 2H, J 11 Hz, ArCH$_2$), 7.402 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

TABLE 7

(Example 6)

| Tetrasialosides | Starting compound | TLC, eluant H, R$_f$ | Aggregate, %* | Yield % |
|---|---|---|---|---|
| [Neu5Ac-Gab-Ad-NHCH$_2$—]$_4$C (37) | (26) | 0.80 | No self-association | 76 |
| [Neu5Ac-Gab-Ad-Gly-NHCH$_2$—]$_4$C (38) | (27) | 0.82 | | 81 |
| [Neu5Ac-Gab-Ad-Gly$_2$-NHCH$_2$—]$_4$C (39) | (28) | 0.81 | | 91 |
| [Neu5Ac-Gab-Ad-Gly$_3$-NHCH$_2$—]$_4$C (40) | (29) | 0.77 | | 90 |
| [Neu5Ac-Gab-Ad-Gly$_4$-NHCH$_2$—]$_4$C (41) | (30) | 0.75 | | 83 |
| [Neu5Ac-Gab-Ad-Gly$_5$-NHCH$_2$—]$_4$C (42) | (31) | 0.71 | | 83 |
| [Neu5Ac-Gab-Ad-AC$_2$-Gly$_5$-NHCH$_2$—]$_4$C (43) | (32) | Monomer and aggregate are eluted separately; monomer: R$_f$ ≈ 0.6 aggregate: R$_f$ ≈ 0 | 6 | 87 |
| [Neu5Ac-Gab-Ad-AC$_3$-Gly$_5$-NHCH$_2$—]$_4$C (44) | (33) | | 54 | 90 |
| [Neu5Ac-Gab-AC-Ad-Gly$_5$-NHCH$_2$—]$_4$C (45) | (34) | | 12 | 93 |
| [Neu5Ac-Gab-AC$_2$-Ad-Gly$_5$-NHCH$_2$—]$_4$C (46) | (35) | | 92 | 86 |
| [Neu5Ac-Gab-AC$_3$-Ad-Gly$_5$-NHCH$_2$—]$_4$C (47) | (36) | | 96 | 89 |

*Determined by means of gel permeation chromatography

[Neu5Ac-Gab-Ad-NHCH$_2$-]$_4$C (37). $^1$H-NMR spectrum in D$_2$O (δ, ppm): matrix: 1.633 (m, 4H, COCH$_2$CH$_2$), 2.293 and 2.358 (m, 4H, 2 COCH$_2$CH$_2$), 2.943 (s, 2H, CCH$_2$), 4.003 (s, 2H, ArNHCOCH$_2$), 4.493 and 4.718 (d, 2H, J 11

[Neu5Ac-Gab-Ad-Gly$_2$-NHCH$_2$-]$_4$C (39). $^1$H-NMR spectrum in D$_2$O (δ, ppm): matrix: 1.626 (m, 4H, COCH$_2$CH$_2$), 2.341 (m, 4H, 2 COCH$_2$CH$_2$), 2.831 (s, 2H, CCH$_2$), 3.894 and 3.991 (s, 4H, 2 CH$_2$$^{Gly1,2}$), 4.022 (s, 2H, ArNH- COC$\underline{H}_2$), 4.492 and 4.719 (d, 2H, J 11 Hz, ArCH$_2$), 7.402 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

[Neu5Ac-Gab-Ad-Gly$_3$-NHCH$_2$-]$_4$C (40). $^1$H-NMR spectrum in D$_2$O (δ, ppm): matrix: 1.631 (m, 4H, COCH$_2$C$\underline{H}_2$), 2.344 (m, 4H, 2 COC$\underline{H}_2$CH$_2$), 2.857 (s, 2H, CCH$_2$), 3.912, 3.931 and 4.024 (s, 6H, 3 CH$_2^{Gly1-3}$), 4.029 (s, 2H, ArNHCOC$\underline{H}_2$), 4.500 and 4.725 (d, 2H, J 11 Hz, ArCH$_2$), 7.408 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

[Neu5Ac-Gab-Ad-Gly$_4$-NHCH$_2$-]$_4$C (41). $^1$H-NMR spectrum in D$_2$O (δ, ppm): matrix: 1.636 (m, 4H, COCH$_2$C$\underline{H}_2$), 2.350 (m, 4H, 2 COC$\underline{H}_2$CH$_2$), 2.864 (s, 2H, CCH$_2$), 3.912, 3.934, 3.968 and 4.025 (s, 8H, 4 CH$_2^{Gly1-4}$), 4.032 (s, 2H, ArNHCOC$\underline{H}_2$), 4.497 and 4.725 (d, 2H, J 11 Hz, ArCH$_2$), 7.408 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

[Neu5Ac-Gab-Ad-Gly$_5$-NHCH$_2$-]$_4$C (42). $^1$H-NMR spectrum in D$_2$O (δ, ppm): matrix: 1.638 (m, 4H, COCH$_2$C$\underline{H}_2$), 2.355 (m, 4H, 2 COC$\underline{H}_2$CH$_2$), 2.878 (s, 2H, CCH$_2$), 3.921, 3.933, 3.974 (x2) and 4.032 (s, 10H, 5 CH$_2^{Gly1-5}$), 4.036 (s, 2H, ArNHCOC$\underline{H}_2$), 4.502 and 4.724 (d, 2H, J 11 Hz, ArCH$_2$), 7.410 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

[Neu5Ac-Gab-Ad-AC$_2$-Gly$_5$-NHCH$_2$-]$_4$C (43). $^1$H-NMR spectrum in D$_2$O (δ, ppm): matrix: 1.286, 1.476 and 1.567 (m, 12H, 6 CH$_2$), 1.623 (m, 4H, COCH$_2$C$\underline{H}_2$C$\underline{H}_2$CH$_2$CO), 2.179 (t, 2H, J 7.4 Hz, CH$_2$CO), 2.245 and 2.367 (m, 4H, COC$\underline{H}_2$CH$_2$CH$_2$C$\underline{H}_2$CO), 2.299 (t, 2H, J 7.4 Hz, CH$_2$CO), 2.882 (s, 2H, CCH$_2$), 3.133 (m, 4H, 2 CH$_2$N), 3.928, 3.940, 3.987 (x2) and 4.043 (x2) (s, 12H, 6 COCH$_2$N), 4.502 and 4.730 (d, 2H, J 11 Hz, ArCH$_2$), 7.418 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

Aggregate [Neu5Ac-Gab-Ad-AC$_3$-Gly$_5$-NHCH$_2$-]$_4$C (44). $^1$H-NMR spectrum in D$_2$O is very similar to the spectrum of compound (43), matrix (δ, ppm): 1.283, 1.476, 1.570 (m, 18H, 9 CH$_2$), 2.178 and 2.189 (t, 2×2H, J 7.4 Hz, 2 CH$_2$CO), 2.301 (t, 2H, J 7.4 Hz, CH$_2$CO), 3.135 (m, 6H, 3 CH$_2$N), 3.928, 3.940, 3.987 (x2) and 4.043 (x2) (s, 12H, 6 COCH$_2$N), 4.502 and 4.730 (d, 2H, J 11 Hz, ArCH$_2$), 7.418 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

[Neu5Ac-Gab-AC-Ad-Gly$_5$-NHCH$_2$-]$_4$C (45). $^1$H-NMR spectrum in D$_2$O (δ, ppm): matrix: 1.334 (m, 2H, CH$_2$), 1.504 (m, 2H, C$\underline{H}_2$CH$_2$NH), 1.569 (m, 4H, COCH$_2$C$\underline{H}_2$CH$_2$CO), 1.625 (m, 2H, C$\underline{H}_2$CH$_2$CO), 2.207 and 2.313 (m, 4H, COC$\underline{H}_2$CH$_2$CH$_2$C$\underline{H}_2$CO), 2.344 (t, 2H, J 7 Hz, CH$_2$CO), 2.885 (s, 2H, CCH$_2$), 3.156 (t, 2H, J7.4 Hz, CH$_2$N), 3.928, 3.942, 3.979, 3.984, 4.037 and 4.042 (s, 12H, 6 COCH$_2$N), 4.506 and 4.729 (d, 2H, J 11 Hz, ArCH$_2$), 7.420 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

Aggregate [Neu5Ac-Gab-AC$_2$-Ad-Gly$_5$-NHCH$_2$-]$_4$C (46). $^1$H-NMR spectrum in D$_2$O (δ, ppm): matrix: 1.268, 1.504 and 1.630 (m, 12H, 6 CH$_2$), 1.572 (m, 4H, COCH$_2$C$\underline{H}_2$C$\underline{H}_2$CH$_2$CO), 2.185 (t, 2H, J 7 Hz, CH$_2$CO), 2.212 and 2.315 (m, 4H, COC$\underline{H}_2$CH$_2$CH$_2$C$\underline{H}_2$CO), 2.349 (t, 2H, J 7.4 Hz, CH$_2$CO), 2.898 (s, 2H, CCH$_2$), 3.130 and 3.158 (t, 2×2H, J 7.4 Hz, 2 CH$_2$N), 3.934, 3.945, 3.987 (x2), 4.039 and 4.045 (s, 12H, 6 COCH$_2$N), 4.509 and 4.725 (d, 2H, J 11 Hz, ArCH$_2$), 7.422 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

Aggregate [Neu5Ac-Gab-AC$_3$-Ad-Gly$_5$-NHCH$_2$-]$_4$C (47). The $^1$H-NMR spectrum in D$_2$O is very similar to the spectrum of compound (46), the signals are in some cases broader. Matrix (δ, ppm): 1.276, 1.461 and 1.630 (m, 18H, 9 CH$_2$), 2.186 (t, 2×2H, J 7 Hz, 2 CH$_2$CO), 2.349 (t, 2H, J 7.4 Hz, CH$_2$CO), 3.132 (m, 6H, 3CH$_2$N), 3.934, 3.945, 3.987 (x2), 4.039 and 4.045 (s, 12H, 6 COCH$_2$N), 4.509 and 4.725 (d, 2H, J 11 Hz, ArCH$_2$), 7.422 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

EXAMPLE 7

Preparation of the Aggregate {[Neu5Acα-OCH$_2$(p-C$_6$H$_4$)NHCOCH$_2$NH—CO(CH$_2$)$_4$CO—(NHCH$_2$CO)$_7$—NHCH$_2$—]$_4$C}, (ammonium salt)

{[Neu5Ac-Gab-Ad-Gly$_7$-NHCH$_2$-]$_4$C}$_x$ (48).

18.8 mg (26 μmol) of the lyophilised compound (15) are added to 6.1 mg (3.25 μmol) of tetrahydrochloride (22a), prepared as described in Example 4, in 0.5 ml of water. The pH of the reaction mixture was adjusted to pH=8 with 1M NaHCO$_3$ solution. The reaction solution was stirred at room temperature for 3 days, the pH being maintained at 8 by the addition of 1M NaHCO$_3$ solution. The reaction mixture was separated over a Sephadex LH-20 column with a 0.05M aqueous NH$_4$OH solution. After concentration and drying in vacuo, 9.6 mg of product (48) were obtained, corresponding to a yield of 71%.

$^1$H-NMR spectrum (D$_2$O, δ, ppm): matrix: 1.638 (m, 4H, COCH$_2$CH$_2$), 2.358 (m, 4H, 2 COCH$_2$CH$_2$), 2.878 (s, 2H, CCH$_2$), 3.918, 3.938, 3.978 (x4) and 4.034 (s, 14H, 7 CH$_2^{Gly1-7}$), 4.037 (s, 2H, ArNHCOCH$_2$), 4.498 and 4.728 (d, 2H, J 11 Hz, ArCH$_2$), 7.408 (m, 4H, Ar). Neu5Acα fragment: 1.680 (dd, 1H, J$_4$ 12 Hz, H-3ax), 2.036 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

EXAMPLE 8

Preparation of Aggregates

Preparation of {Galα1-3Galβ1-O(CH$_2$)$_3$NH—CO(CH$_2$)$_4$CO—(NH(CH$_2$)$_5$CO)$_3$—(NHCH$_2$CO)$_5$—NHCH$_2$-]$_4$C}$_x$ {[B$_{di}$-Ap-Ad-AC$_3$-Gly$_5$-NHCH$_2$-]$_4$C}$_x$ (49).

15.6 mg of (16) and 5 μl of Et$_3$N were added to a suspension von 5.6 mg (2 μmol) of tetrahydrochloride (25a), prepared as described in Example 4, in 0.5 ml of DMSO. The reaction solution was stirred at 40° C. for 3 days. After the addition of 0.2 ml of conc. NH$_4$OH solution, the reaction mixture was stirred for 30 minutes and separated over a Sephadex LH-20 column with MeCN/H$_2$O 1:1. After concentration and drying in vacuo, 6.4 mg of product (49) were obtained, corresponding to a yield of 69%.

$^1$H-NMR spectrum (D$_2$O/CD$_3$OC 2:1, δ, ppm): 1.374, 1.562 and 1.645 (m, CH$_2$), 1.883 (m, 2H, OCH$_2$CH$_2$CH$_2$N), 2.265 (t, 4H, J 7.5 Hz, 2 CH$_2$CO), 2.292 (m, 4H, 2 CH$_2$CO), 2.377 (t, 2H, J 7.5 Hz, CH$_2$CO), 2.955 (br. s, CCH$_2$), 3.213 (t, 6H, 3 CH$_2$N), 3.348 (m, 2H, OCH$_2$CH$_2$CH$_2$N), 3.697 (dd, 1H, H-2 Galβ), 3.756 (m, OCHCH$_2$CH$_2$N), 3.910 (dd, 1H, J$_3$ 10 Hz, H-2 Galα), 4.00, 4.046 and 4.097 (s, 10H, 5 COCH$_2$N), 4.205 (d, 1H, J$_3$ 3 Hz, H-4 Galβ), 4.255 (m, 1H, H-5 Galα), 4.462 (d, 1H, J$_2$ 8 Hz, H-1 Galβ), 5.184 (d, 1H, J$_2$ 4 Hz, H-1 Galα).

Preparation of {[Neu5Acα2-3Galβ1-4Glcβ1-NHCOCH$_2$NH—CO(CH$_2$)$_4$CO—(NHCH$_2$CO)$_5$—NHCH$_2$-]$_4$C}$_x$ {[3'SL-NHCOCH$_2$NH-Ad-Gly$_5$-NHCH$_2$-]$_4$C}$_x$ (50) was prepared starting from (21a) and (14) analogously to compound (49).

TLC: R$_f$ 0.52 (methanol/acetonitrile/water 6:6:3). Yield 65%.

$^1$H-NMR spectrum (D$_2$O, δ, ppm): 1.622 (m, 4H, CH$_2$C H$_2$CH$_2$CO), 1.797 (dd, 1H, J$_4$ 12 Hz, H-3$_{ax}$ Neu5Ac), 2.017 (s, 3H, COCH$_3$), 2.342 (m, 4H, 2 CH$_2$CO), 2.744 (dd, 1H, J$_{3ax}$ 12.5 Hz, J$_4$ 4.6 Hz, H-3$_{eq}$ Neu5Ac), 2.895 (br. s, CCH$_2$), 3.452 (dd, 1H, H-2 Glcβ), 3.568 (dd, 1H, J$_3$ 10 Hz, H-2 Galβ), 3.954, 3.992 and 4.041 (s, 12H, 6 COCH$_2$N), 4.105 (dd, 1H, J$_2$ 10 Hz, J$_4$ 3 Hz, H-3 Galβ), 4.523 (d, 1H, J$_2$ 8 Hz, H-1 Galβ), 5.005 (d, 1H, J$_2$ 9 Hz, H-1 Glcβ).

Preparation of {[Neu5Acα2-3Galβ1-4Glcβ1-NHCOCH$_2$NH—CO(CH$_2$)$_4$CO—(NHCH$_2$CO)$_7$—NHCH$_2$-]$_4$C}$_x$ {[3'SL-NHCOCH$_2$NH-Ad-Gly$_7$-NHCH$_2$-]$_4$C}$_x$ (51) was prepared analogously to compound (48) starting from (22a) and (14). Yield 78%.

$^1$H-NMR spectrum (D$_2$O, δ, ppm): 1.622 (m, 4H, CH$_2$C H$_2$CH$_2$CO), 1.797 (dd, 1H, J$_4$ 12 Hz, H-3$_{ax}$ Neu5Ac), 2.017 (s, 3H, COCH$_3$), 2.342 (m, 4H, 2 CH$_2$CO), 2.744 (dd, 1H, J$_{3ax}$ 12.5 Hz, J$_4$ 4.6 Hz, H-3$_{eq}$ Neu5Ac), 2.895 (br. s, CCH$_2$), 3.452 (dd, 1H, H-2 Glcβ), 3.568 (dd, 1H, J$_3$ 10 Hz, H-2 Galβ), 3.954, 3.992 and 4.041 (s, 16H, 8 COCH$_2$N), 4.105 (dd, 1H, J$_2$ 10 Hz, J$_4$ 3 Hz, H-3 Galβ), 4.523 (d, 1H, J$_2$ 8 Hz, H-1 Galβ), 5.005 (d, 1H, J$_2$ 9 Hz, H-1 Glcβ).

EXAMPLE 9

Induction of Self-association of [HCl.H-Gly$_7$-NHCH$_2$-]$_4$C (22a)

The investigation into the light scattering of a 50 mM solution of compound (22a) in water was carried out using a Spectra-Physics 164 argon laser (plasma lines λ=528.7 and 611.5 nm), the scattering was measured at an angle of 90° to the incident light beam. The particle size thereby determined was <2.5 nm. 50 μl of 0.8M NaHCO$_3$ solution were added to the resulting solution. The light scattering was measured, as described above, the average particle size thereby determined was 200-400 nm.

50 μl of a 0.8M HCl was added to the resulting solution, and the sample was investigated by means of light scattering, as described above. The particle size thereby determined was <2.5 nm.

EXAMPLE 10

Inhibition of the Viral Cell Adhesion of Influenza Viruses

The specific binding constants of the inhibitor virus complexes were determined by means of a fetuin binding assay, as described in the literature (U.S. Pat. No. 5,571,836, 1996; PCT WO 98/14215).

TABLE 8

Example 10
Influenza virus A/NIB/44/90M H3N2

| Inhibitor | Compound No. | K$_d$, μM |
|---|---|---|
| Neu5Acα-OBn | | 100 |
| [Neu5Ac-Gab-Ad-Gly$_n$-NHCH$_2$—]$_4$C (n = 0-5) | (38)-(42) | ~50 |
| [Neu5Ac-Gab-Ad-Gly$_7$-NHCH$_2$—]$_4$C | (48) | 0.1 |
| [Neu5Ac-Ap-Ad-Gly$_n$-NHCH$_2$—]$_4$C (n = 0-3) | | 200 |
| [Neu5Ac-Gab-AC-Ad-Gly$_5$-NHCH$_2$—]$_4$C | (45) | 7 |
| [Neu5Ac-Gab-AC$_2$-Ad-Gly$_5$-NHCH$_2$—]$_4$C | (46) | 0.3 |
| [Neu5Ac-Gab-AC$_3$-Ad-Gly$_5$-NHCH$_2$—]$_4$C | (47) | 0.1 |
| [Neu5Ac-Gab-Ad-AC$_2$-Gly$_5$-NHCH$_2$—]$_4$C | (43) | 0.1 |
| [Neu5Ac-Gab-Ad-AC$_3$-Gly$_5$-NHCH$_2$—]$_4$C | (44) | 0.04 |
| Influenza virus A/Duck/Alberta/60/67 H12N5 | | |
| 3'SL | | 20 |
| [3'SL-NHCOCH$_2$NH-Ad-Gly$_5$-NHCH$_2$—]$_4$C | (50) | 1 |
| [3'SL-NHCOCH$_2$NH-Ad-Gly$_7$-NHCH$_2$—]$_4$C | (51) | 0.1 |

EXAMPLE 11

Inhibition of the complement-dependent cytotoxicity of human blood sera with respect to PK 15 cells as a result of the aggregate {[B$_{di}$-Ap-Ad-AC$_3$-Gly$_5$-NHCH$_2$-]$_4$C}$_x$ (49)

Serial dilutions of the B disaccharide Galα1-3Gal and of the aggregate {[B$_{di}$-Ap-Ad-AC$_3$-Gly$_5$-NHCH$_2$-]$_4$C}$_x$ (49) with human blood serum were incubated at 4° C. overnight, and the inhibition of the cytotoxicity was demonstrated, as described in the literature (R. Rieben, E. von Allmen, E. Y. Korchagina, U. E. Nydegger, F. A. Neethling, M. Kujundzic, E. Koren, N. V. Bovin, D. K. C. Cooper, *Xenotransplantation*, 2, 98, 1995). After the addition of the complement constituents in the form of 10% rabbit serum (Sigma), the samples were incubated for 10 minutes with PK15 cells grown on Terasaki plates. The cells were then washed and stained using a cytotoxicity kit ("live/dead" viability/cytotoxicity kit, Molecular Probes, Eugene, Oreg., USA). By measuring the fluorescence intensities, the live/dead proportions were determined. The inhibition of cytotoxicity was calculated by comparison with a serum sample to which no inhibitor had been added. In the case of the following concentrations (calculated as molar concentration of the B disaccharide units), 50% inhibition of cytotoxicity was achieved:

Galα1-3Gal (B disaccharide) 200 μM $\{[B_{di}\text{-Ap-Ad-AC}_3\text{-Gly}_5\text{-NHCH}_2\text{-}]_4 C\}_x$ aggregate (49) 0.5 μM

EXAMPLE 12

The divalent matrices of the formula $[\text{HCl.H-Gly}_n\text{-NHCH}_2\text{CH}_2\text{-}]_2$ (n=2, 4) were prepared starting from 1,4-diaminobutane analogously to the synthesis in Example 4.

Preparation of bis-1,4-(hexaglycilamido)-butane [HCl.H-Gly$_6$-NHCH$_2$CH$_2$-]$_2$ (52).

48 mg of BocGlyGlyNOS (146 μmol) and 0.1 ml of Et$_3$N were added to a solution of 30 mg of the compound [HCl.H-Gly$_4$-NHCH$_2$CH$_2$-]$_2$ (48.6 μmol) in 0.5 ml of DMSO. The reaction mixture was stirred at room temperature for 24 hours, a precipitate being formed. After the addition of 1 ml of water, the precipitate was separated off by centrifugation, suspended three times in 1 ml of MeOH each time and again centrifuged. After drying in vacuo, 0.5 ml of trifluoroacetic acid was added to the residue. After two hours, 3 ml of toluene were twice added and the solution concentrated. The residue was dissolved in water and, after the addition of 0.1 ml of a 2M HCl solution, evaporated to dryness. The product was obtained by means of gel chromatography over a Sephadex LH-20 column (1×30 cm) with a 50% aqueous acetonitrile solution. After freeze-drying of the product fraction, 26 mg (63%) of compound (52) were obtained.

$^1$H-NMR spectrum in D$_2$O (δ, ppm): 1.455 (m, 4H, CH$_2$C H$_2$CH$_2$CH$_2$), 3.172 (m, 4H, 2CH$_2$N), 3.856, 3.872, 3.947, 3.960, 3.975 and 4.028 (s, 2H, COCH$_2$N).

The aggregate {[Neu5Acα-OCH$_2$(p-C$_6$H$_4$)NHCOCH$_2$NH—CO(CH$_2$)$_4$CO—(NHCH$_2$CO)$_6$—NHCH$_2$CH$_2$—]$_2$}$_x$ (ammonium salt) {[Neu5Ac-Gab-Ad-Gly$_6$-NHCH$_2$CH$_2$-]$_2$}$_x$ (53) was prepared analogously to compound (48) in Example 7.

Yield 72% $^1$H-NMR spectrum in D$_2$O (δ, ppm): matrix: 1.470 (m, 4H, CH$_2$CH$_2$CH$_2$CH$_2$), 1.649 (m, 4H, COCH$_2$C H$_2$), 2.363 (m, 4H, 2COCH$_2$CH$_2$), 3.181 (m, 4H, 2CH$_2$N), 3.869, 3.941, 3.962, 3.977 (x3) and 4.045 (s, 2H, COCH$_2$N), 4.505 and 4.727 (d, 2H, J 11 Hz, ArCH$_2$), 7.415 (m, 4H, Ar). Neu5Acα fragment: 1.680 (dd, 1H, J$_4$ 12 Hz, H-3ax), 2.086 (s, 3H, NAc), 2.778 (dd, 1H, J$_{3ax}$ 12.5 Hz, J$_4$ 4.6 Hz, H-3eq), 3.598 (dd, 1H, J$_8$ 9 Hz, H-7), 3.636 (dd, 1H, J$_8$ 6 Hz, H-9b), 3.695 (ddd, 1H, J$_5$ 9.8 Hz, H-4), 3.728 (dd, 1H, J$_7$ 1.5 Hz, J$_5$ 10.2 Hz, H-6), 3.782 (ddd, 1H, H-8), 3.822 (dd, 1H, H-5), 3.846 (dd, 1H, J$_{9b}$ 12 Hz, J$_8$ 2.3 Hz, H-9a).

EXAMPLE 13

Preparation of NeuAcα2-6Galβ1-4GlcNAcβ-O(CH$_2$)$_3$NH—CO(CH$_2$)$_4$COO(p-C$_6$H$_4$NO$_2$) 6'-SLN-Ap-Ad-ONp (52)

A solution of 65 mg (195 μmol) of di-(4-nitrophenyl) adipate (3) in 300 μl of DMF was added to a solution of 28 mg (38 μmol) of the compound 6'SLN-O(CH$_2$)$_3$NH$_2$ in 400 μl of DMSO. The mixture was stirred at 20° C. for 16 hours. After the addition of 5 ml of H$_2$O and 0.1 ml of AcOH, the excess (3) was filtered off. The filtrate was concentrated to a small volume of about 1 ml and separated by means of gel permeation chromatography over Sephadex LH-20 (MeCN/H$_2$O/AcOH 1:1:0.005).

Yield (52)—71%. TLC: R$_f$ 0.46 (i-PrOH/acetone/H$_2$O 4:3:2). $^1$H-NMR spectrum (D$_2$O, δ, ppm): 1.641 (m, 6H, 2 COCH$_2$CH$_2$ and OCH$_2$CH$_2$), 1.674 (dd, 1H, H-3-ax Neu5Ac), 1.930 and 1.958 (s, 2×3H, 2 COCH$_3$, Neu5Ac and GlcNAc), 2.218 (t, 2H, NCOCH$_2$), 2.559 (dd, 1H, J$_{3ax}$, 13 Hz, J$_4$ 4.7 Hz, H-3eq Neu5Ac), 2.646 (m, 2H, CH$_2$COOAr), 3.090 and 3.190 (m, 2×1H, NCH$_2$), 3.42-3.94 (21H, overlapping of the carbohydrate signals and OCH$_2$), 4.328 (d, 1H, J$_2$ 8 Hz, H-1 Gal), 4.419 (d, 1H, J$_2$ 8 Hz, H-1 GlcNAc), 7.291 and 8.256 (d, 2×2H, J 8.3 Hz, Ar).

Preparation of [6'SLN-Ap-Ad-Gly$_7$-NHCH$_2$]$_4$C (53)

15 mg (16.2 μmol) of the compound NeuAcα2-6Galβ1-4GlcNAcβ-O(CH$_2$)$_3$NH-CO(CH$_2$)$_4$COO(p-C$_6$H$_4$NO$_2$) (52) were added to a solution of 5 mg (2.7 μmol) of the tetrahydrochloride [HCl Gly$_7$-NHCH$_2$-]$_4$C (22a) in 500 μl of H$_2$O. The pH value of the resulting solution was adjusted to pH~8 by the dropwise addition of 1M NaHCO$_3$. The reaction mixture was stirred at room temperature for 3 days and separated by means of gel permeation chromatography (G10, 0.05M NH$_3$).

Yield (53) 34%, TLC: R$_f$~0 (i-PrOH/acetone/H$_2$O 4:3:2). $^1$H-NMR spectrum (D$_2$O, δ, ppm): matrix: 1.628 (m, 4H, COCH$_2$CH$_2$) 1.789 (m, 2H, OCH$_2$CH$_2$), 2.275 and 2.373 (m, 2×2H, 2 COCH$_2$CH$_2$), 2.935 (s, 2H, CCH$_2$), 3.197 and 3.279 (m, 2×1H, NCH$_2$), 3.971, 3.990, 4.026 (x3) and 4.077 (x2) (s, 14H, 7 CH$_2^{Gly1-7}$). Carbohydrate signals: 1.730 (dd, 1H, H-3ax Neu5Ac), 2.049 and 2.078 (s, 2×3H, 2 COCH$_3$, Neu5Ac and GlcNAc), 2.693 (dd, 1H, J$_{3ax}$ 12.4 Hz, J$_4$ 4.6 Hz, H-3eq Neu5Ac), 3.54-3.96 (21 H, overlapping of the carbohydrate signals and OCH$_2$), 4.468 (d, 1H, J$_2$ 8 Hz, H-1 Gal), 4.562 (d, 1H, J$_2$ 8 Hz, H-1 GlcNAc).

The compound [6'-SLN-Ap-Ad-AC$_2$-Gly$_5$-NHCH$_2$]$_4$C (54) was prepared in an analogous manner starting from the tetrahydrochloride [HCl.H-AC$_2$-Gly$_5$-NHCH$_2$]$_4$C (24a) and NeuAcα2-6Galβ1-4GlcNAcβ-O(CH$_2$)$_3$NH—CO(CH$_2$)$_4$COO(p-C$_6$H$_4$NO$_2$) (52). Yield (54)—63%. TLC: R$_f$~0 (i-PrOH/acetone/H$_2$O 4:3:2).

$^1$H-NMR spectrum in D$_2$O (δ, ppm): matrix: 1.341, 1.524 and 1.631 (m, 12H, 6 CH$_2$), 1.599 (m, 4H, COCH$_2$CH$_2$C H$_2$CH$_2$CO), 1.785 (m, 2H, OCH$_2$CH$_2$), 2.238 (t, 2H, J 7.4 Hz, CH$_2$CO), 2.260 (m, 4H, COCH$_2$CH$_2$CH$_2$CH$_2$CO), 2.349 (t, 2H, J 7.5 Hz, CH$_2$CO), 2.929 (s, 2H, CCH$_2$), 3.182 (broad t, 4H, J 6.6 Hz, 2 CH$_2$N), 3.195 and 3.275 (m, 2×1H, NCH$_2$), 3.979, 4.022 (x3) and 4.073 (s, 10H, 5 COCH$_2$N). Carbohydrate signals: see (53).

TABLE 9

Example 13
Inhibition of the viral time-adhesion of influenza viruses;
strain A/NIB/H1N1/89M, FBI text [see Table 1], 6'SLN as reference compound.

| Inhibitor | Compound No. | Relative activity |
|---|---|---|
| 6'SLN | | 1 |
| (Neu5Ac-Gab-Ad-$Gly_7$-$NHCH_2$—$]_4C$ | (48) | <0.2 |
| [6'SLN-Ap-Ad-$Gly_7$-$NHCH_2]_4C$ | (53) | 100 |
| [6'SLN-Ap-Ad-$AC_2$-$Gly_5$-$NHCH_2]_4C$ | (54) | 1000 |

Comparison Example 1

The compound of formula {Neu5Acα2-6Galβ1-4GlcNAcβ1-$NHCOCH_2NH$—$CO(CH_2)_4CO$—$(NHCH_2CO)_3$—$NHCH_2$—$\}_4C$, which is known from Example 7 of WO 98/14215, does not form aggregates according to the invention, as has been demonstrated by the following methods:

1. In thin-layer chromatography only a single compound, the monomer, can be observed under the following conditions. Traces of aggregates are completely absent: silica gel 60 TLC plates, catalogue no. 1.05724, Merck; eluant: i-PrOH/acetone/$H_2O$ 4:3:2; observation: charring after immersion in 7% $H_3PO_4$.
2. The $^1$H-NMR spectrum (Bruker 500 MHz, $D_2O$, 300 K) of the compound does not exhibit any line broadening that would be characteristic of glycopeptide aggregates.
3. Laser light-scattering experiments (Coulter Submicron Model N4MD, He-Ne laser, I 632.8) on the compound in aqueous solution do not give any indication of the formation of aggregates.
4. Using gel permeation HPLC (TSK-4000 column, 0.2M NaCl), only one peak is observed, which corresponds to the molecular weight of the monomer.
5. The activity of the compound in the inhibition of influenza viruses (A/NIB/23/89M H1N1, A/NIB/44/90M H3N2, B/NIB/15/89M, FBI test) is comparable with that of 6'SLN trisaccharide, whereas typical associated glycopeptides, such as, for example, the $Gly_7$ analogon) are more active by factors of ten.

It is therefore clear that the compound known from the prior art is fundamentally different from the compounds of the present invention. The demonstrated functional difference is based on the structural difference of the fragment K, which is not suitable for intermolecular association because the number of chain segments suitable for the formation of hydrogen bridges is too small.

The invention claimed is:

1. A compound of the general formula (I)

$$X(B)_m \quad (I)$$

wherein

X is C or CH and

B are identical or different and denote K-R, wherein

K is a bond or is $A^1$—$(A^2$—$A^3)_k$-sp, wherein $A^1$ is $(CH_2)_tY(CH_2)_u$, wherein Y is >C═O, >NH, —O—, —S— or a bond, t is an integer from 0 to 6 and u is an integer from 0 to 6, $(A^2$—$A^3)$ can be any $A^2$ and any $A^3$ in any combination, $A^2$ is —NHCO— or —CONH—, $A^3$ is $(CH_2)_r$, $O(CH_2)_r$, or $S(CH_2)_r$, wherein r=1, sp is a divalent spacer or a bond, and k is an integer from 5 to 100, and R is hydrogen, sialic acid, sialyl lactose, sialyl lactosamine, lactose, mannose, Galα1-3Gal, Galα1-3(Fucα1-2)Gal,GalNAcα1-3(Fucα1-2)Gal, Neu5Acα2-6GalNAc, $SiaLe^A$, $SiaLe^X$, $HSO_3Le^A$, $HSO_3Le^X$, Galα1-3Galβ1-4GlcNAc, Galα1-3Galβ1-4Glc, Neu5Acα2-6Galβ1-4GlcNAc, $HSO_3$GlcAβ1-3Galβ1-4GlcNAc, N-acetyl-lactosamine or polylactosamine, sialic acid benzyl glycoside, $HSO_3$GlcAβ1-3Gal, $HSO_3$GlcAβ1-3Galβ1-4GlcNAcβ1-3Galβ1-4Glc, GalNAcα, GalNAcα1-3(Fucα1-2)Galβ1-4GlcNAc, Galα1-3(Fucα1-2)Galβ1-4GlcNAc, $HSO_3(Sia)Le^X$, $HSO_3(Sia)Le^A$, $Le^Y$, GlcNAcβ1-6(GlcNAcβ1-3)Galβ1-4Glc, GalNAcβ1-4(Neu5Acα2-3)Galβ1-4Glc, mannose-6-phosphate, GalNAcβ1-4GlcNAc, oligosialic acid, N-glycolylneuraminic acid, Galα1-4Galβ1-4Glc, or Galα1-4Galβ1-4GlcNAc; and m is at least 2, with the proviso that (1) in the compound at least three R are not hydrogen, (2) there are at least two K that are not a bond, and (3) X, B and m are so selected that an intermolecular association of the K in liquid phase by the formation of hydrogen bonds is possible, with formation of aggregates that present on the surface a plurality of R that are not hydrogen, and (4) the molar mass of the fragment $X(K)_m$ is less than 20,000.

2. A compound of the general formula (I)

$$X(B)_m \quad (I)$$

wherein

X is C or CH and

B are identical or different and denote K-R, wherein

K is a bond or is $A^1$—$(A^2$—$A^3)_k$-sp, wherein $A^1$ is $(CH_2)_tY(CH_2)_u$, wherein Y is >C═O, >NH, —O—, —S— or a bond, t is an integer from 0 to 6 and u is an integer from 0 to 6, $(A^2$—$A^3)$ can be any $A^2$ and any $A^3$ in any combination, $A^2$ is —NHCO— or —CONH—, $A^3$ is $(CH_2)_r$, $O(CH_2)_r$, or $S(CH_2)_r$, wherein r=1, sp is a divalent spacer or a bond, and k is an integer from 5 to 100, and R is hydrogen, sialic acid, sialyl lactose, sialyl lactosamine, lactose, mannose, Galα1-3Gal, Galα1-3(Fucα1-2)Gal, GalNAcα1-3(Fucα1-2)Gal, Neu5Acα2-6GalNAc, $SiaLe^A$, $SiaLe^X$, $HSO_3Le^A$, $HSO_3Le^X$, Galα1-3Galβ1-4GlcNAc, Galα1-3Galβ1-4Glc, Neu5Acα2-6Galβ1-4GlcNAc, $HSO_3$GlcAβ1-3Galβ1-4GlcNAc, N-acetyl-lactosamine or polylactosamine, sialic acid benzyl glycoside, $HSO_3$GlcAβ1-3Gal, $HSO_3$GlcAβ1-3Galβ1-4GlcNAcβ1-3Galβ1-4Glc, GalNAcα, GalNAcα1-3(Fucα1-2)Galβ1-4GlcNAc, Galα1-3(Fucα1-2)Galβ1-4GlcNAc, $HSO_3(Sia)Le^X$, $HSO_3(Sia)Le^A$, $Le^Y$, GlcNAcβ1-6(GlcNAcβ1-3)Galβ1-4Glc, GalNAcβ1-4(Neu5Acα2-3)Galβ1-4Glc, mannose-6-phosphate, GalNAcβ1-

4GlcNAc, oligo-sialic acid, N-glycolylneuraminic acid, Galα1-4Galβ1-4Glc, or Galα1-4Galβ1-4GlcNAc; and m is 3 or 4, with the proviso that
(1) in the compound at least three R are not hydrogen,
(2) X, B and m are so selected that an intermolecular association of the K in liquid phase is possible, especially under aqueous conditions, by the formation of hydrogen bonds, with formation of aggregates, and
(3) the molar mass of the fragment $X(K)_m$ is less than 20,000.

3. A compound according to claim 2 wherein the molecular mass of the fragment $X(K)_m$ is less than 4000.

4. A compound of the general formula (I)

$$X(B)_m \quad (I)$$

wherein

X is $CH_{4-m}$ and

B are identical or different and denote K-R, wherein

K is a bond or is $A^1$—$(A^2$—$A^3)_k$-sp, wherein $A^1$ $CH_2$, wherein

Y is >C=O, >NH, —O—, —S— or a bond, ($A^2$—$A^3$) can be any $A^2$ and any $A^3$ in any combination, $A^2$ is NHCO, $A^3$ is $CH_2$, wherein sp is $(CH_2)_3CONHCH_2CONHC_6H_4$-4-$CH_2O$—, and k is 8, and R is Neu5Acα2-6Galβ1-4GlcNAc; and m is an integer from 2 to 4, with the proviso that
(1) in the compound at least one R is not hydrogen,
(2) there are at least two K that are not a bond, and
(3) X, B and m are so selected that an intermolecular association of the K in liquid phase by the formation of hydrogen bonds is possible, with formation of aggregates that present on the surface a plurality of R that are not hydrogen, and
(4) the molar mass of the fragment $X(K)_m$ is less than 20,000.

5. An aggregate of the general formula (II):

$$\{X(B)_m\}_n \quad (II)$$

wherein $X(B)_m$ may be identical or different and denote a compound of the general formula (I), $$X(B)_m \quad (I)$$

wherein

X is C or CH and

B are identical or different and denote K-R, wherein

K is a bond or is $A^1$—$(A^2$—$A^3)_k$-sp, wherein $A^1$ is $(CH_2)_tY(CH_2)_u$, wherein Y is >C=O, >NH, —O—, —S— or a bond, t is an integer from 0 to 6 and u is an integer from 0 to 6, ($A^2$—$A^3$) can be any $A^2$ and any $A^3$ in any combination, $A^2$ is —NHCO— or —CONH—, $A^3$ is $(CH_2)_r$, $O(CH_2)_r$, or $S(CH_2)_r$, wherein r=1, sp is a divalent spacer or a bond, and k is an integer from 5 to 100, and R is hydrogen, sialic acid, sialyl lactose, sialyl lactosamine, lactose, mannose, Galα1-3Gal, Galα1-3(Fucα1-2)Gal, GalNAcα1-3(Fucα1-2)Gal, Neu5Acα2-6GalNAc, SiaLe$^A$, SiaLe$^X$, HSO$_3$Le$^A$, HSO$_3$Le$^X$, Galα1-3Galβ1-4GlcNAc, Galα1-3Galβ1-4Glc, Neu5Acα2-6Galβ1-4GlcNAc, HSO$_3$GlcAβ1-3Galβ1-4GlcNAc, N-acetyl-lactosamine or polylactosamine, sialic acid benzyl glycoside, HSO$_3$GlcAβ1-3Gal, HSO$_3$GlcAβ1-3Galβ1-4GlcNAcβ1-3Galβ1-4Glc, GalNAcα, GalNAcα1-3(Fucα1-2)Galβ1-4GlcNAc, Galα1-3(Fucα1-2)Galβ1-4GlcNAc, HSO$_3$(Sia)Le$^X$, HSO$_3$(Sia)Le$^A$, Le$^Y$, GlcNAcβ1-6(GlcNAcβ1-3)Galβ1-4Glc, GalNAcβ1-4(Neu5Acα2-3)Galβ1-4Glc, mannose-6-phosphate, GalNAcβ1-4GlcNAc, oligo-sialic acid, N-glycolylneuraminic acid, Galα1-4Galβ1-4Glc, or Galα1-4Galβ1-4GlcNAc; and m is 3 or 4, with the proviso that
(1) in the compound at least three R are not hydrogen,
(2) there are at least two K that are not a bond, and
(3) X, B and m are so selected that an intermolecular association of the K in liquid phase by the formation of hydrogen bonds is possible, with formation of aggregates that present on the surface a plurality of R that are not hydrogen, and
(4) the molar mass of the fragment $X(K)_m$ is less than 20,000, and n is from 2 to 100,000, and wherein $X(B)_m$ are non-covalently bonded.

6. An aggregate according to claim 5 having a leaf-like, linear, cyclic, polycyclic, polyhedral, spherical or dendritic structure.

7. An aggregate according to claim 5 of two or more different compounds comprising a compound of the general formula (I)

$$X(B)_m \quad (I)$$

wherein

X is C or CH and

B are identical or different and denote K-R, wherein

K is a bond or is $A^1$—$(A^2$—$A^3)_k$-sp, wherein $A^1$ is $(CH_2)_tY(CH_2)_u$, wherein Y is >C=O, >NH, —O—, —S— or a bond, t is an integer from 0 to 6 and u is an integer from 0 to 6, ($A^2$—$A^3$) can be any $A^2$ and any $A^3$ in any combination, $A^2$ is —NHCO— or —CONH—, $A^3$ is $(CH_2)_r$, $O(CH_2)_r$, or $S(CH_2)_r$, wherein r=1, sp is a divalent spacer or a bond, and k is an integer from 5 to 100, and R is hydrogen, sialic acid, sialyl lactose, sialyl lactosamine, lactose, mannose, Galα1-3Gal, Galα1-3(Fucα1-2)Gal, GalNAcα1-3(Fucα1-2)Gal, Neu5Acα2-6GalNAc, SiaLe$^A$, SiaLe$^X$, HSO$_3$Le$^A$, HSO$_3$Le$^X$, Galα1-3Galβ1-4GlcNAc, Galα1-3Galβ1-4Glc, Neu5Acα2-6Galβ1-4GlcNAc, HSO$_3$GlcAβ1-3Galβ1-4GlcNAc, N-acetyl-lactosamine or polylactosamine, sialic acid benzyl glycoside, HSO$_3$GlcAβ1-3Gal, HSO$_3$GlcAβ1-3Galβ1-4GlcNAcβ1-3Galβ1-4Glc, GalNAcα, GalNAcα1-3(Fucα1-2)Galβ1-4GlcNAc, Galα1-3(Fucα1-2)Galβ1-4GlcNAc, HSO$_3$(Sia)Le$^X$, HSO$_3$(Sia)Le$^A$, Le$^Y$, GlcNAcβ1-6(GlcNAcβ1-3)Galβ1-4Glc, GalNAcβ1-4(Neu5Acα2-3)Galβ1-4Glc, mannose-6-phosphate, GalNAcβ1-4GlcNAc, oligo-sialic acid, N-glycolylneuraminic acid, Galα1-4Galβ1-4Glc, or Galα1-4Galβ1-4GlcNAc; and m is 3 or 4, with the proviso that
  (1) in the compound at least three R are not hydrogen,
  (2) there are at least two K that are not a bond, and
  (3) X, B and m are so selected that an intermolecular association of the K in liquid phase by the formation of hydrogen bonds is possible, with formation of aggregates that present on the surface a plurality of R that are not hydrogen, and
  (4) the molar mass of the fragment $X(K)_m$ is less than 20,000.

8. A method of preparing an aggregate comprising: preparing a compound of the general formula (II)

$$\{X(B)_m\}_n \qquad (II)$$

wherein
  $X(B)_m$ may be identical or different and denote a compound of the general formula (I), $$X(B)_m \qquad (I)$$

wherein
  X is C or CH and
  B are identical or different and denote K-R, wherein
  K is a bond or is $A^1-(A^2-A^3)_k$-sp, wherein
    $A^1$ is $(CH_2)_t Y(CH_2)_u$, wherein
      Y is >C=O, >NH, —O—, —S— or a bond,
      t is an integer from 0 to 6 and
      u is an integer from 0 to 6,
    $(A^2-A^3)$ can be any $A^2$ and any $A^3$ in any combination,
    $A^2$ is —NHCO— or —CONH—,
    $A^3$ is $(CH_2)_r$, $O(CH_2)_r$, or $S(CH_2)_r$, wherein
      r=1,
    sp is a divalent spacer or a bond, and
    k is an integer from 5 to 100, and
  R is hydrogen, sialic acid, sialyl lactose, sialyl lactosamine, lactose, mannose, Galα1-3Gal, Galα1-3(Fucα1-2)Gal, GalNAcα1-3(Fucα1-2)Gal, Neu5Acα2-6GalNAc, SiaLe$^A$, SiaLe$^X$, HSO$_3$Le$^A$, HSO$_3$Le$^X$, Galα1-3Galβ1-4GlcNAc, Galα1-3Galβ1-4Glc, Neu5Acα2-6Galβ1-4GlcNAc, HSO$_3$GlcAβ1-3Galβ1-4GlcNAc, N-acetyl-lactosamine or polylactosamine, sialic acid benzyl glycoside, HSO$_3$GlcAβ1-3Gal, HSO$_3$GlcAβ1-3Galβ1-4GlcNAcβ1-3Galβ1-4Glc, GalNAcα, GalNAcα1-3(Fucα1-2)Galβ1-4GlcNAc, Galα1-3(Fucα1-2)Galβ1-4GlcNAc, HSO$_3$(Sia)Le$^X$, HSO$_3$(Sia)Le$^A$, Le$^Y$, GlcNAcβ1-6(GlcNAcβ1-3)Galβ1-4Glc, GalNAcβ1-4(Neu5Acα2-3)Galβ1-4Glc, mannose-6-phosphate, GalNAcβ1-4GlcNAc, oligo-sialic acid, N-glycolylneuraminic acid, Galα1-4Galβ1-4Glc, or Galα1-4Galβ1-4GlcNAc; and
  m is 3 or 4,
with the proviso that
  (1) in the compound at least three R are not hydrogen,
  (2) there are at least two K that are not a bond, and
  (3) X, B and m are so selected that an intermolecular association of the K in liquid phase by the formation of hydrogen bonds is possible, with formation of aggregates that present on the surface a plurality of R that are not hydrogen, and
  (4) the molar mass of the fragment $X(K)_m$ is less than 20,000, and
  n is from 2 to 100,000,
and wherein $X(B)_m$ are non-covalently bonded.

9. A method according to claim 8, further comprising adding a concentrated salt solution, changing the pH or the temperature, or adding organic solvents.

10. A method according to claim 8 further comprising increasing the specific physiological activities of molecules by incorporating a radical R into a compound of the general formula (I).

11. A method for changing the structure of an aggregate of the general formula (II)

$$\{X(B)_m\}_n \qquad (II)$$

wherein $X(B)_m$ may be identical or different and denote a compound of the general formula (I)

$$X(B)_m \qquad (I)$$

wherein
  X is C or CH and
  B are identical or different and denote K-R, wherein
  K is a bond or is $A^1-(A^2-A^3)_k$-sp, wherein
    $A^1$ is $(CH_2)_t Y(CH_2)_u$, wherein
      Y is >C=O, >NH, —O—, —S— or a bond,
      t is an integer from 0 to 6 and
      u is an integer from 0 to 6,
    $(A^2-A^3)$ can be any $A^2$ and any $A^3$ in any combination,
    $A^2$ is —NHCO— or —CONH—,
    $A^3$ is $(CH_2)_r$, $O(CH_2)_r$, or $S(CH_2)_r$, wherein
      r=1,
    sp is a divalent spacer or a bond, and
    k is an integer from 5 to 100, and
  R is hydrogen, sialic acid, sialyl lactose, sialyl lactosamine, lactose, mannose, Galα1-3Gal, Galα1-3(Fucα1-2)Gal, GalNAcα1-3(Fucα1-2)Gal, Neu5Acα2-6GalNAc, SiaLe$^A$, SiaLe$^X$, HSO$_3$Le$^A$, HSO$_3$Le$^X$, Galα1-3Galβ1-4GlcNAc, Galα1-3Galβ1-4Glc, Neu5Acα2-6Galβ1-4GlcNAc, HSO$_3$GlcAβ1-3Galβ1-4GlcNAc, N-acetyl-lactosamine or polylactosamine, sialic acid benzyl glycoside, HSO$_3$GlcAβ1-3Gal, HSO$_3$GlcAβ1-3Galβ1-4GlcNAcβ1-3Galβ1-4Glc, GalNAcα, GalNAcα1-3(Fucα1-2)Galβ1-4GlcNAc, Galα1-3(Fucα1-2)Galβ1-4GlcNAc, HSO$_3$(Sia)Le$^X$, HSO$_3$(Sia)Le$^A$, Le$^Y$, GlcNAcβ1-6(GlcNAcβ1-3)Galβ1-4Glc, GalNAcβ1-4(Neu5Acα2-3)Galβ1-4Glc, mannose-6-phosphate, GalNAcβ1-4GlcNAc, oligo-sialic acid, N-glycolylneuraminic acid, Galα1-4Galβ1-4Glc, or Galα1-4Galβ1-4GlcNAc; and
  m is 3 or 4,
with the proviso that
  (1) in the compound at least three R are not hydrogen,
  (2) there are at least two K that are not a bond, and
  (3) X, B and m are so selected that an intermolecular association of the K in liquid phase by the formation of hydrogen bonds is possible, with formation of aggregates that present on the surface a plurality of R that are not hydrogen, and
  (4) the molar mass of the fragment $X(K)_m$ is less than 20,000 and
  n is from 2 to 100,000,
and wherein $X(B)_m$ are non-covalently bonded,
further comprising adding a concentrated salt solution, changing the temperature or the pH and/or adding urea, trifluoroethanol or peptides.

12. A method of preparing a therapeutic drug comprising: preparing the compound of the general formula (I)

$$X(B)_m \qquad (I)$$

wherein
  X is C or CH and
  B are identical or different and denote K-R, wherein K is a bond or is $A^1$—$(A^2$—$A^3)_k$-sp, wherein
  $A^1$ is $(CH_2)_tY(CH_2)_u$, wherein
    Y is >C=O, >NH, —O—, —S— or a bond,
    t is an integer from 0 to 6 and
    u is an integer from 0 to 6,
  $(A^2$—$A^3)$ can be any $A^2$ and any $A^3$ in any combination,
  $A^2$ is —NHCO— or —CONH—,
  $A^3$ is $(CH_2)_r$, $O(CH_2)_r$, or $S(CH_2)_r$, wherein
    r=1,
  sp is a divalent spacer or a bond, and
  k is an integer from 5 to 100, and
R is hydrogen, sialic acid, sialyl lactose, sialyl lactosamine, lactose, mannose, Galα1-3Gal, Galα1-3(Fucα1-2)Gal, GalNAcα1-3(Fucα1-2)Gal, Neu5Acα2-6GalNAc, SiaLe$^A$, SiaLe$^X$, HSO$_3$Le$^A$, HSO$_3$Le$^X$, Galα1-3Galβ1-4GlcNAc, Galα1-3Galβ1-4Glc, Neu5Acα2-6Galβ1-4GlcNAc, HSO$_3$GlcAβ1-3Galβ1-4GlcNAc, N-acetyl-lactosamine or polylactosamine, sialic acid benzyl glycoside, HSO$_3$GlcAβ1-3Gal, HSO$_3$GlcAβ1-3Galβ1-4GlcNAcβ1-3Galβ1-4Glc, GalNAcα, GalNAcα1-3(Fucα1-2)Galβ1-4GlcNAc, Galα1-3(Fucα1-2)Galβ1-4GlcNAc, HSO$_3$(Sia)Le$^X$, HSO$_3$(Sia)Le$^A$, Le$^Y$, GlcNAcβ1-6(GlcNAcβ1-3)Galβ1-4Glc, GalNAcβ1-4(Neu5Acα2-3)Galβ1-4Glc, mannose-6-phosphate, GalNAcβ1-4GlcNAc, oligo-sialic acid, N-glycolylneuraminic acid, Galα1-4Galβ1-4Glc, or Galα1-4Galβ1-4GlcNAc; and
m is 3 or 4,
with the proviso that
  (1) in the compound at least three R are not hydrogen,
  (2) there are at least two K that are not a bond, and
  (3) X, B and m are so selected that an intermolecular association of the K in liquid phase by the formation of hydrogen bonds is possible, with formation of aggregates that present on the surface a plurality of R that are not hydrogen, and
  (4) the molar mass of the fragment $X(K)_m$ is less than 20,000; or
preparing the compound of the general formula (II):

$$\{X(B)_m\}_n \quad (II)$$

wherein
$X(B)_m$ may be identical or different and denote a compound of the general formula (I), and
  n is from 2 to 100,000,
and wherein $X(B)_m$ are non-covalently bonded; and
a pharmaceutically acceptable carrier.

13. A method of treating diseases arising from inflammation, viral and bacterial infections, influenza viruses, selectin-mediated inflammatory processes, tumour metastases, or in the neutralisation of antibodies in autoimmune disorders and transplants; said method comprising administering a compound of the general formula (I)

$$X(B)_m \quad (I)$$

wherein
X is C or CH and
B are identical or different and denote K-R, wherein
K is a bond or is $A^1$—$(A^2$—$A^3)_k$-sp, wherein
  $A^1$ is $(CH_2)_tY(CH_2)_u$, wherein
    Y is >C=O, >NH, —O—, —S— or a bond,
    t is an integer from 0 to 6 and
    u is an integer from 0 to 6,
  $(A^2$—$A^3)$ can be any $A^2$ and any $A^3$ in any combination,
  $A^2$ is —NHCO— or —CONH—,
  $A^3$ is $(CH_2)_r$, $O(CH_2)_r$, or $S(CH_2)_r$, wherein
    r=1,
  sp is a divalent spacer or a bond, and
  k is an integer from 5 to 100, and
R is hydrogen, sialic acid, sialyl lactose, sialyl lactosamine, lactose, mannose, Galα1-3Gal, Galα1-3(Fucα1-2)Gal, GalNAcα1-3(Fucα1-2)Gal, Neu5Acα2-6GalNAc, SiaLe$^A$, SiaLe$^X$, HSO$_3$Le$^A$, HSO$_3$Le$^X$, Galα1-3Galβ1-4GlcNAc, Galα1-3Galβ1-4Glc, Neu5Acα2-6Galβ1-4GlcNAc, HSO$_3$GlcAβ1-3Galβ1-4GlcNAc, N-acetyl-lactosamine or polylactosamine, sialic acid benzyl glycoside, HSO$_3$GlcAβ1-3Gal, HSO$_3$GlcAβ1-3Galβ1-4GlcNAcβ1-3Galβ1-4Glc, GalNAcα, GalNAcα1-3(Fucα1-2)Galβ1-4GlcNAc, Galα1-3(Fucα1-2)Galβ1-4GlcNAc, HSO$_3$(Sia)Le$^X$, HSO$_3$(Sia)Le$^A$, Le$^Y$, GlcNAcβ1-6(GlcNAcβ1-3)Galβ1-4Glc, GalNAcβ1-4(Neu5Acα2-3)Galβ1-4Glc, mannose-6-phosphate, GalNAcβ1-4GlcNAc, oligo-sialic acid, N-glycolylneuraminic acid, Galα1-4Galβ1-4Glc, or Galα1-4Galβ1-4GlcNAc; and
m is 3 or 4,
with the proviso that
  (1) in the compound at least three R are not hydrogen,
  (2) there are at least two K that are not a bond, and
  (3) X, B and m are so selected that an intermolecular association of the K in liquid phase by the formation of hydrogen bonds is possible, with formation of aggregates that present on the surface a plurality of R that are not hydrogen, and
  (4) the molar mass of the fragment $X(K)_m$ is less than 20,000; or
administering an aggregate of the general formula (II)

$$\{X(B)_m\}_n \quad (II)$$

wherein
$X(B)_m$ may be identical or different and denote a compound of the general formula (I), and
  n is from 2 to 100,000,
and wherein $X(B)_m$ are non-covalently bonded.

14. A method according to claim 13 further comprising preparing functionalized molecular surfaces.

* * * * *

UNITED STATES PATENT AND TRADEMARK OFFICE
CERTIFICATE OF CORRECTION

PATENT NO. : 7,294,615 B1 Page 1 of 1
APPLICATION NO. : 10/019902
DATED : November 13, 2007
INVENTOR(S) : Bovin et al.

It is certified that error appears in the above-identified patent and that said Letters Patent is hereby corrected as shown below:

On Title Page:

Item (73) Assignees: Please correct to read as follows:
    Nikolai Vladimirovich Bovin, Moskow (RU)
    Alexander Borisovich Tusikov, Moskow (RU)
    Alexander Alexandrovich Chinarev, Moskow (RU)
    Maria Alexandravona Dicusar, Moskow (RU)
    Alexandra Sergeevna Gambarian, Moskow (RU)
    Valentina Petrovna Marinina, Moskow (RU)

Title Page Col. 2, line 7, Item (56) Foreign Patent Documents:
                                    Please correct: "WO WO 98/142015 * 4/1998"
                                        to read -- WO WO 98/14215 * 4/1998 --

Signed and Sealed this

Fifteenth Day of April, 2008

JON W. DUDAS
*Director of the United States Patent and Trademark Office*